United States Patent [19]

Fried

[11] 4,456,768

[45] Jun. 26, 1984

[54] CHEMICAL SYNTHESIS

[75] Inventor: Josef Fried, Chicago, Ill.

[73] Assignee: The University of Chicago, Chicago, Ill.

[21] Appl. No.: 259,740

[22] Filed: May 1, 1981

Related U.S. Application Data

[63] Continuation of Ser. No. 195,291, Oct. 8, 1980, Pat. No. 4,324,730, which is a continuation of Ser. No. 83,398, Oct. 10, 1979, abandoned, which is a continuation of Ser. No. 108,525, Dec. 31, 1979, abandoned.

[51] Int. Cl.$^3$ .................. C07C 177/00; A61K 31/557
[52] U.S. Cl. ...................................... 562/503; 560/27; 560/53; 560/60; 560/62; 560/121; 562/463; 562/470; 562/472; 564/47; 564/57; 564/90; 564/98; 564/169; 564/171; 564/189; 564/442; 564/454

[58] Field of Search ...................... 560/121, 53, 60, 62, 560/27; 562/503, 463, 470, 472; 542/429; 564/442, 454, 189, 169, 171, 47, 57, 96, 98; 568/380, 336, 645, 775, 838

[56] References Cited

U.S. PATENT DOCUMENTS 4,044,043 8/1977 Bernady .............................. 560/121

OTHER PUBLICATIONS

Grieco et al., J. Org. Chem. 44, 2189, 2194, (1979).
Nakai, Chemistry Letters, 1499 (1979).

*Primary Examiner*—Robert Gerstl

[57] ABSTRACT

Prostaglandin and prostacyclin compounds which are fluorine substituted in any one or more of the following positions 4,4; 7,7; 10,10; and 5.

5 Claims, No Drawings

CHEMICAL SYNTHESIS

The invention described herein was made in the course of work done under a grant or award from the United States Department of Health Education and Welfare.

This application is a continuation application of my prior filed copending application Ser. No. 195,291, filed Oct. 8, 1980, U.S. Pat. No. 4,324,730 which in turn is a continuation application of my prior filed applications Ser. No. 83398, filed Oct. 10, 1979 now abandoned and Ser. No. 108,525 filed Dec. 31, 1979 now abandoned.

This invention relates to and has as its objective the production of pharmacologically active prostaglandin and prostacyclin compounds which possess a chemical structure whereby they are fluorine substituted in any one or more of the following positions on the molecule 4,4; 7,7; 10,10; and 5.

In general, prostaglandin and prostacyclin compounds are those organic compounds possessing generic chemical structures which may be characterized as possessing the following basic skeletal structural formulae derived from prostanoic acid:

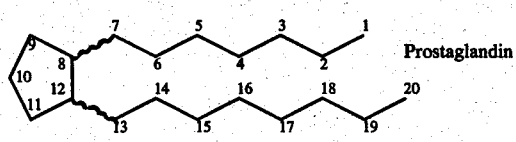

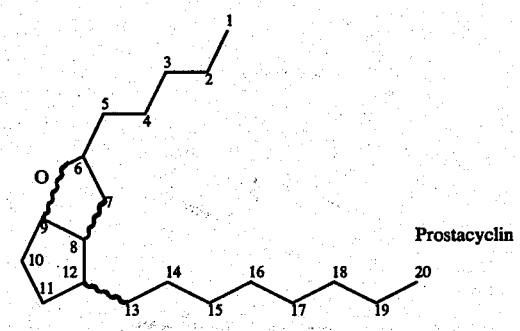

There are many variant substituents and modifications which may be incorporated in the generic chemical structures of these compounds to yield a myriad of specific prostaglandin and prostacyclin compounds as is well known to the skilled worker. For example, reference may be had to the following U.S. Pat. Nos.: 4,124,599; 4,158,667; 4,174,441; 4,198,430; 4,211,706; 4,211,713; 4,211,714, the teachings and disclosures of which are incorporated herein by reference. Reference may also be had to pages 1019–1020 Merck Index, 9th Edition.

The compounds of this invention may be generically characterized as prostaglandin and prostacyclin compounds whose chemical structures from the $C_4$ to $C_{12}$ positions of the molecule may be represented by the following formulae:

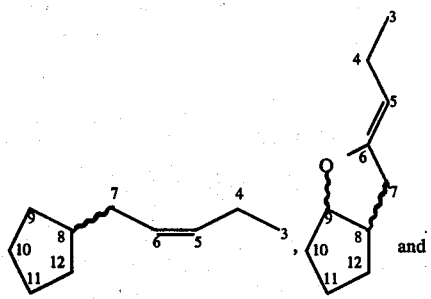

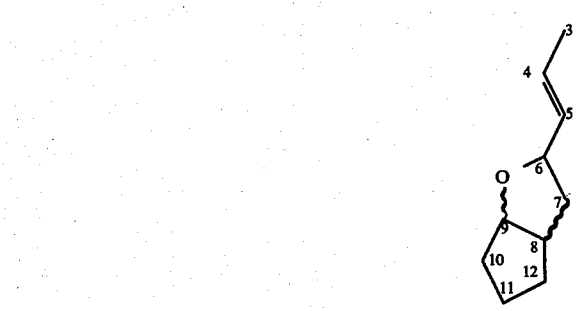

The remaining positions of the molecule of the respective prostaglandin and prostacyclin compounds of this invention may be comprised of those substituents as are well known to and understood by the skilled worker, as more specifically set forth hereinafter.

More particularly, it is a specific objective of this invention to produce useful prostaglandin and prostacyclin compounds possessing chemical structural configurations from the $C_4$ to $C_{12}$ positions which may be represented by the following formulae:

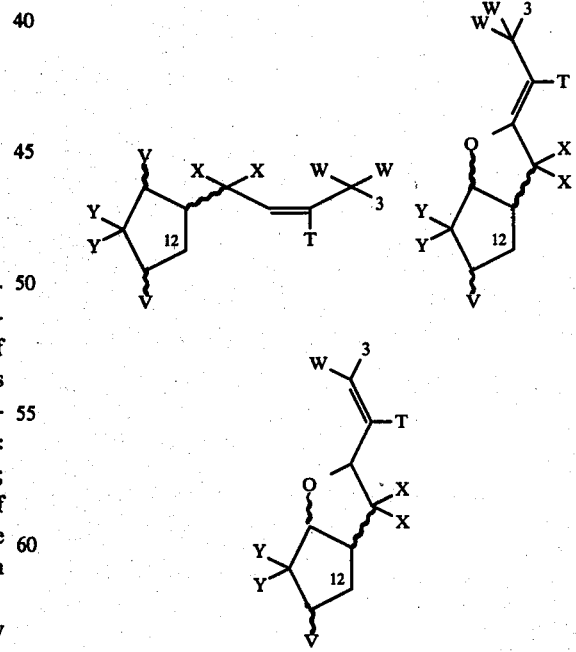

wherein Y, X, T and W may be H or F, with the proviso that at least one of Y, X, T and W must be F; and wherein V may be H, OH, acyloxy and alkoxy.

More particularly, this invention relates to the production of prostaglandin and prostacyclin compounds possessing the following general chemical structures:

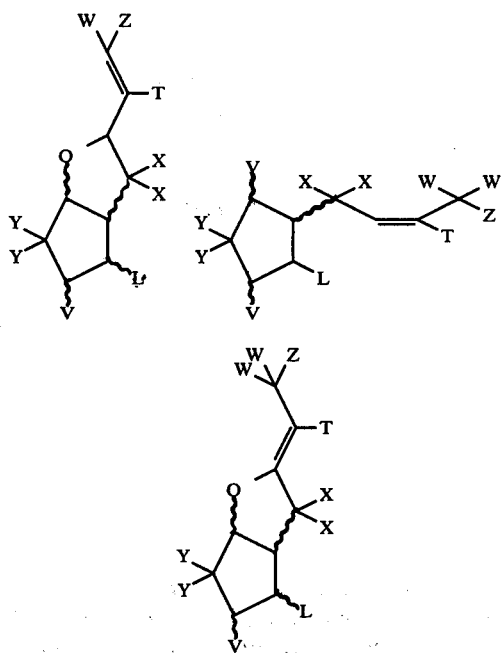

wherein Y, T, W, and X may each be H or F; provided that at least one of Y, T, W, and X is F;

L may be any side chain which is known in the art to be part of and incorporable in the respective prostaglandin or prostacyclin compound involved, for example, those side chains which are disclosed and taught to the skilled worker in Belgian Pat. No. 851,122, U.S. Pat. No. 4,110,532, U.S. Pat. No. 4,158,667, U.S. Pat. No. 4,191,824, U.S. Pat. No. 4,124,599 and U.S. Pat. No. 4,174,441 to be possible to incorporate in the said compounds, the teachings and disclosures of which patents are incorporated herein by specific reference thereto;

Z may also be any side chain which is known in the art to be part of and be possible of incorporation in the respective prostaglandin or prostacyclin compound involved, for example, those side chains which are disclosed and taught to the skilled worker in Belgian Pat. No. 851,122, U.S. Pat. No. 4,110,532, U.S. Pat. No. 4,124,599, U.S. Pat. No. 4,158,667, U.S. Pat. No. 4,191,824, and U.S. Pat. No. 4,174,441 to be possible to incorporate in the said compounds, the teachings and disclosures of which patents are incorporated herein by specific reference; and V may also be any substituent which is known in the art and by the skilled worker to be present at those positions in prostaglandin and prostacyclin compounds as is taught and disclosed to the skilled worker by various prior art publications, such as Belgian Pat. No. 851,122, U.S. Pat. No. 4,110,532, U.S. Pat. No. 4,124,500, U.S. Pat. No. 4,158,667, U.S. Pat. No. 4,191,824, and U.S. Pat. No. 4,174,441, which teachings and disclosures are incorporated hereby by specific reference.

More specifically, included in the practice of this invention are compounds of the above structures wherein V may be hydrogen, hydroxy, acyloxy, lower alkyl, hydroxy lower alkyl, or oxo; Z may be $-Z_1-E$, wherein $Z_1$ is $(CH_2)_g-CH_2-CH_2$, or $-(CH_2)_g-O-CH_2-$, or $-(CH_2)_g-CH_2-CF_2-$, or trans—$(CH_2)_g-CH=CH$; wherein g is 0, 1 or 2; and E is $-COOX_1$, wherein $X_1$ is hydrogen, alkyl, cycloalkyl, aralkyl, phenyl, phenyl substituted with chloro or alkyl, an alkali metal or a substituted ammonium cation; or

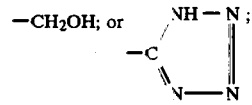

or $-CH_2NL_2L_3$, wherein $L_2$ or $L_3$ are hydrogen, alkyl or $-COOX_1$ wherein $X_1$ is as defined above; $-COL_4-$ wherein $L_4$ is (a) amino of the formula $-NR_{21}R_{22}$, wherein $R_{21}$ and $R_{22}$ are hydrogen, alkyl of 1 to 12 carbon atoms inclusive aralkyl of 7 to 12 carbon atoms inclusive, phenyl, phenyl substituted with 1,2 or 3 chloro or alkyl substituents of 1 to 3 carbon atoms inclusive, or phenyl substituted with hydroxy carbonyl or alkoxy carbonyl of 1 to 4 carbon atoms inclusive; or (b) carbonylamino of the formula $-NR_{23}COR_{21}$, wherein $R_{23}$ is hydrogen or alkyl of 1 to 4 carbon atoms and $R_{21}$ is as defined above; or (c) sulfonylamino of the formula $-NR_{23}SO_2R_{21}$, wherein $R_{21}$ and $R_{23}$ are as defined above; or $-COOL_5$, wherein $L_5$ is p-substituted phenyl selected from the group consisting of:

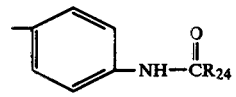

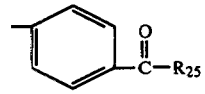

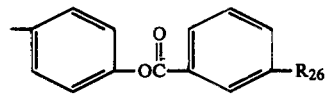

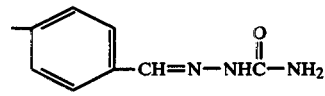

wherein $R_{24}$ is methyl, phenyl, acetamidophenyl, benzamidophenyl or $-NH_2$; $R_{25}$ is methyl, phenyl, $-NH_2$, or methoxy; and $R_{26}$ is hydrogen or acetamido; and L is

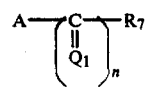

wherein n is 1 or 2; and A is trans—$CH=CH-$, or cis—$CH=CH-$, or $-CH_2-CH_2-$, or $-C\equiv C-$, or trans—$CH-C$(Halogen)—; and $\overset{\|}{Q_1}$ is $R_3\diagup\cdots R_4$, $R_3\cdots\diagdown R_4$ or a mixture of -continued

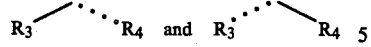

wherein $R_3$ and $R_4$ may be H, OH, alkoxy, acyloxy, or fluoro with the proviso that one of $R_3$ and $R_4$ is fluoro only when the other is fluoro or hydrogen and when taken together $R_3$ and $R_4$ is oxo; and $R_7$ may be (a) $-(CH_2)_g-CH_3$, wherein g is 3, 4 or 5;

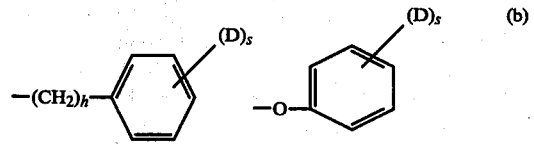

wherein h is 0 or 1; s is 0, 1, 2 or 3; and D is chloro, fluoro, trifluoromethyl, alkyl of one to 3 carbon atoms, inclusive or with the proviso that not more than two D's are other than alkyl and the 1,5- and 1,15-lactones thereof; or (c) $-CH_2OCH=CH-CH_2CH_3$; and Y, T, W and X may each be H or F, provided that at least one of Y, T, W or X is F.

Even more particularly, this invention relates to the production of compounds of the formulae:

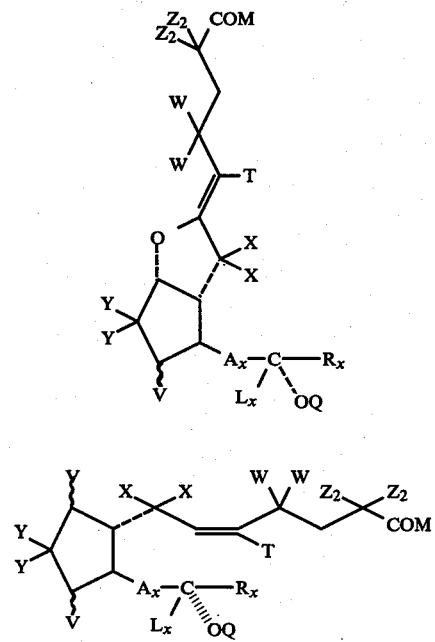

-continued

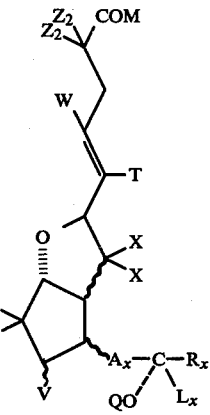

wherein Y, X, T and W may be H or F; provided that at least one of Y, X, T or W must be F; each V may be H, OH, acyloxy or alkoxy; $Z_2$ may be H or F; $A_x$ may be $-CH_2-CH_2-$, $-CH=CH-$ or $-C\equiv C-$; Q may be H, acyl or alkyl; $L_x$ may be H or alkyl; $R_x$ may be alkyl, alkenyl, aralkyl, substituted alkyl or substituted aralkyl; M may be $OR_1$ wherein $R_1$ is H, alkyl, aralkyl, an alkali metal or a substituted ammonium cation, or such other substituent which is known to the skilled worker to be present or incorporable in such prostaglandin or prostacyclin compounds.

Most specifically, this invention relates to the production and use of compounds of the formulae:

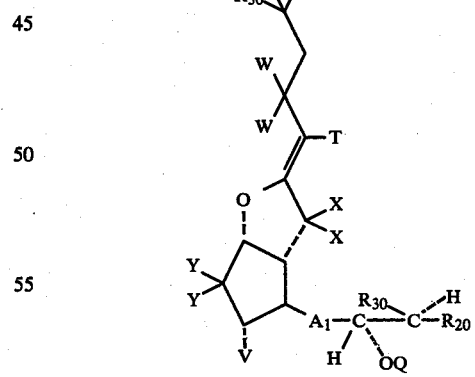

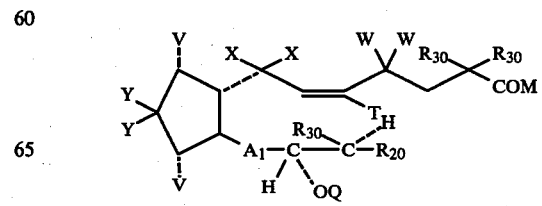

-continued

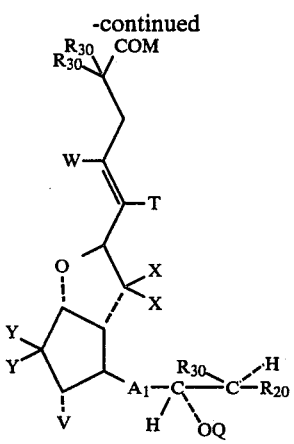

wherein A is —CH=CH or —C≡C—; $R_{30}$ is F or H; $R_{20}$ is lower alkyl, lower alkenyl, aralkyl or substituted aralkyl; M, Q, V, W, X, Y and T are as hereinbefore defined.

In a most preferable embodiment of the instant invention, $A_1$ is C≡C; Y, W, X and T are H or F; Q is H; $R_{30}$ is H or F; $R_{20}$ is lower alkyl; V is H or OH; and M is $OR_1$ wherein $R_1$ is lower alkyl or an alkali metal, for example, sodium.

The compounds of this invention are physiologically active compounds which possess prostacyclin-like activity. Thus, the products of this invention may be employed for the purpose of lowering elevated blood pressure and of increasing peripheral blood flow. Therefore, the products of this invention may be employed in the treatment of hypertension or for the relief of circulatory problems.

In addition, the compounds of this invention prevent the aggregation of blood platelets thereby removing one of the contributory factors to the formation of atherosclerotic plaques. As a result the products of this invention may be employed prophylactically in patients with a tendency of coronary infarcts. In addition, the products of this invention may be employed in hemodialysis and during open heart surgery where it is important to prevent aggregation of platelets thereby impeding the flow of blood through the filter pads.

In addition, some of the products of this invention cause regression of the corpus luteum, and they can therefore be used for estrus synchronization in farm animals so as to achieve greater economy in the practice of artificial insemination, or as contraceptive agents in the human female. Being protected from metabolic inactivation these compounds can be administered perorally or intravenously, in contrast to the corresponding natural prostaglandins.

In addition, some of the products of this invention have been found to be resistant to the action of the major prostaglandin inactivating enzyme, 15-hydroxyprostaglandin dehydrogenase. Such failure to be destroyed in the body has the effect of prolonging or enhancing the action of these substances when compared with the naturally occurring prostaglandins.

In addition, and perhaps one of the most important properties of the products of this invention is the considerable chemical stability which is imparted to them by the presence of the fluorine substituents the 4,4; 7,7; 10,10; or 5 positions. As a result of this greatly increased chemical stability the products of this invention retain their biological activity considerably longer than is the case with the naturally occurring prostacyclins.

The pharmacologically active compounds of this invention may be administered to the animal or patient being treated therewith in any manner known and convenient to the skilled worker practicing the invention, the dosage and concentration of the final products being adjusted to the requirement of the patient and the properties of the respective compound being employed. The skilled worker may prepare the final products in such compositions and dosage forms as are usually employed for such purposes, depending upon the route of administration selected for the ultimate composition, for example, parenteral, peroral or topical final dosage and routes of administration.

It should be understood in the practice of this invention that in the preparation of the various compounds producible thereby, whenever a compound having free hydroxy groups is produced it may be further treated in accordance with methods well known in the art to provide the respective acyl derivatives thereof. Thus, a compound of this invention having free hydroxy groups may be treated with a suitable acylating agent, such as those derived from hydrocarbon carboxylic acids of twelve carbon atoms or less to yield the desired acyloxy derivatives as is well known to the skilled worker.

The products of this invention are prepared by the processes of this invention which entail a number of steps beginning with cyclopentane-1,3-dione as the starting material. The steps involved in the processes of this invention may be generally represented by the following sequence of chemical structures, wherein R', X', and M' are as defined herein.

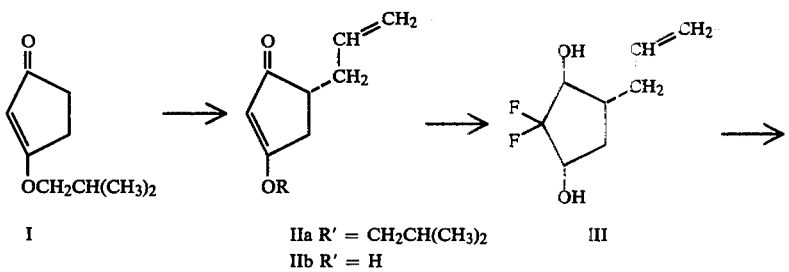

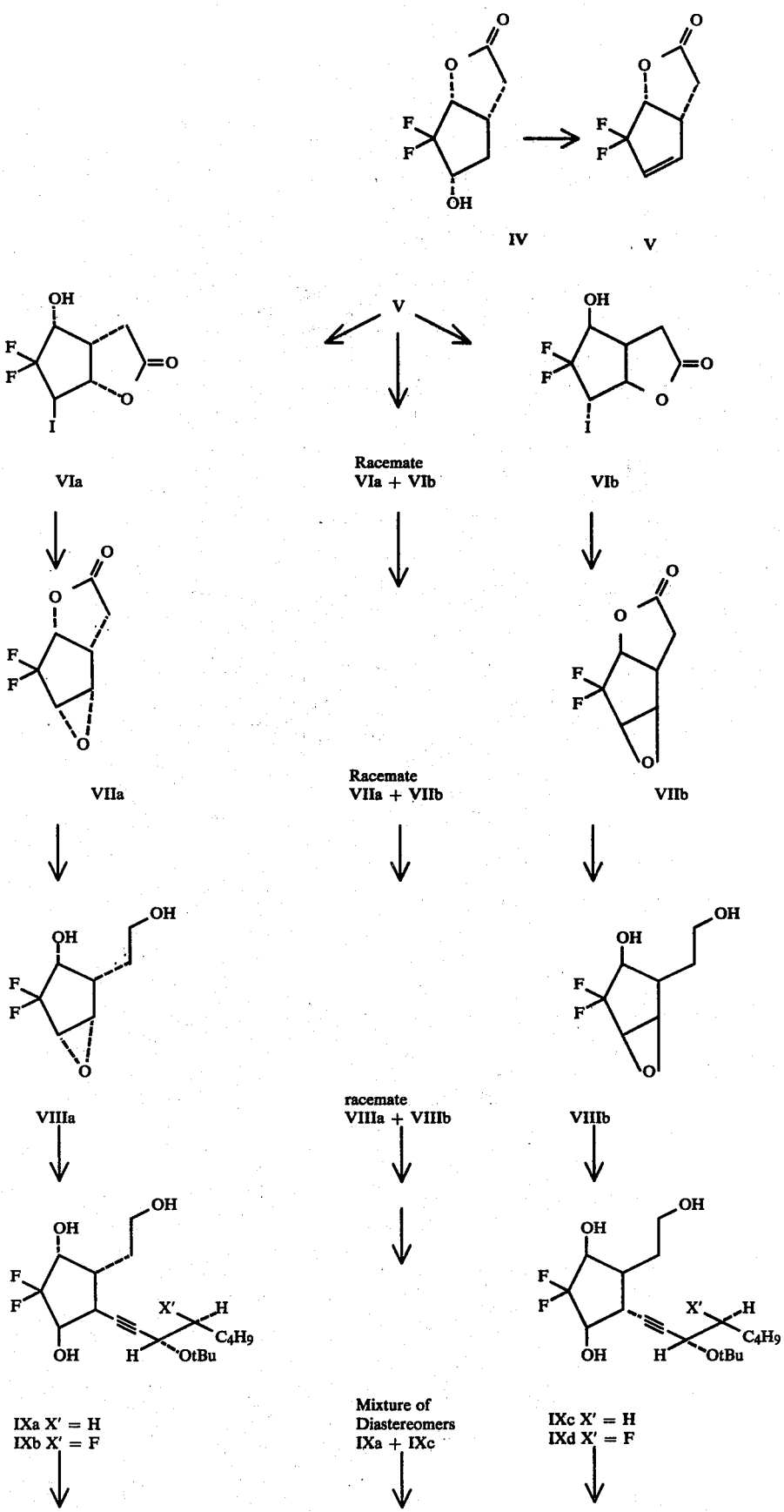

-continued
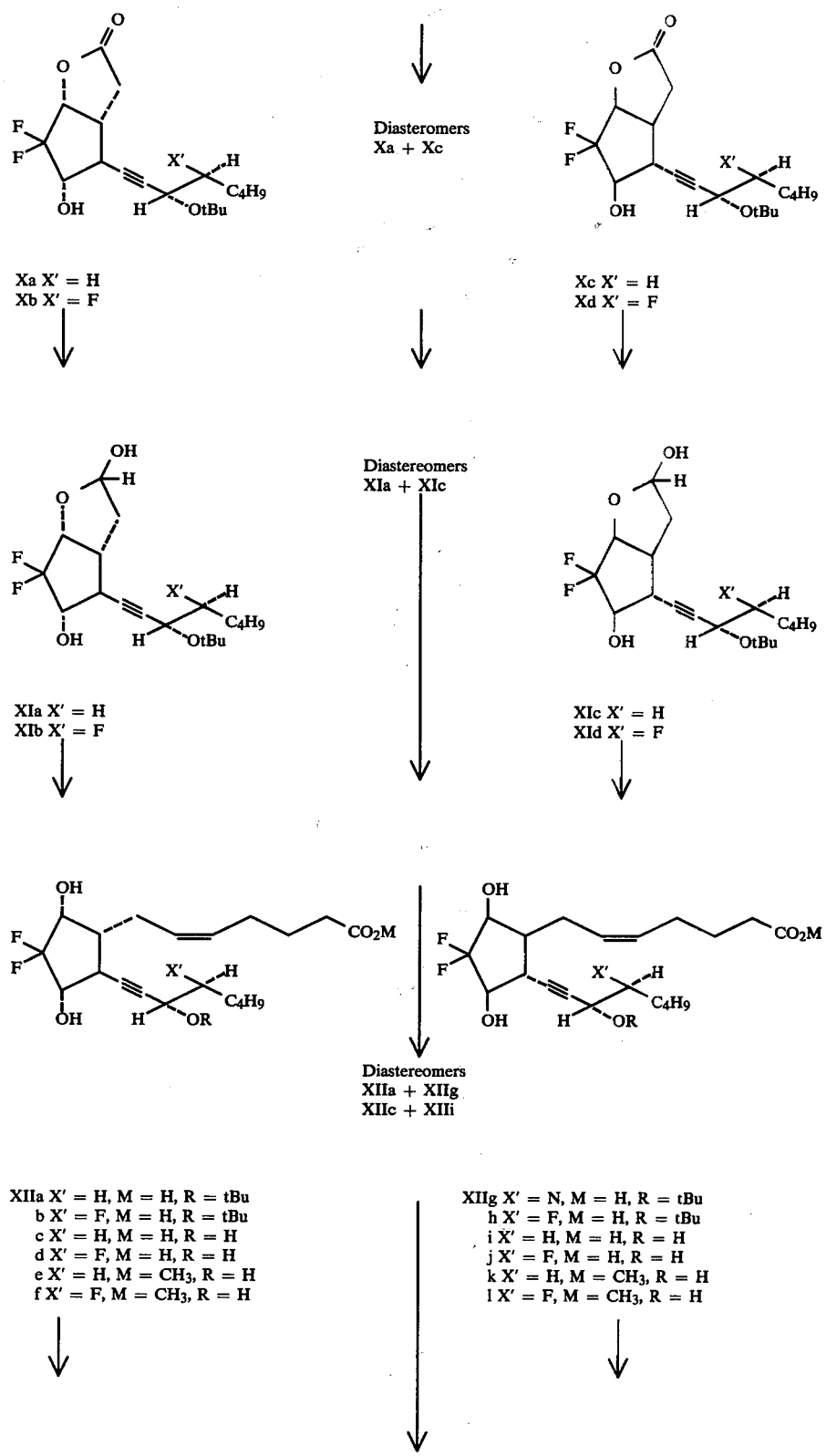
Diasteromers
Xa + Xc
Diastereomers
XIa + XIc
Diastereomers
XIIa + XIIg
XIIc + XIIi
XIIa X' = H, M = H, R = tBu
b X' = F, M = H, R = tBu
c X' = H, M = H, R = H
d X' = F, M = H, R = H
e X' = H, M = CH₃, R = H
f X' = F, M = CH₃, R = H
XIIg X' = N, M = H, R = tBu
h X' = F, M = H, R = tBu
i X' = H, M = H, R = H
j X' = F, M = H, R = H
k X' = H, M = CH₃, R = H
l X' = F, M = CH₃, R = H -continued

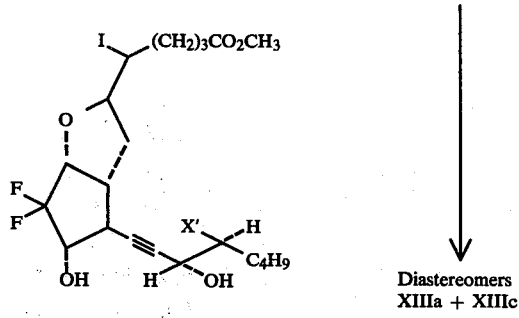

XIIIa X' = H
  b X' = F

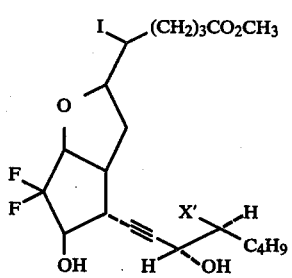

XIIIc X' = H
   d X' = F

Diastereomers
XIIIa + XIIIc

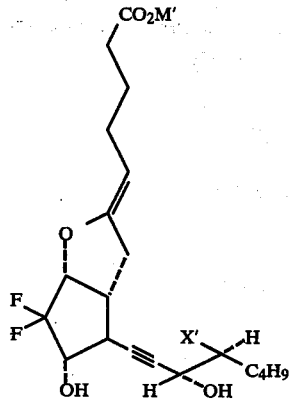

XIVa X' = H, M' = CH₃
  b X' = H, M' = Na
  c X' = F, M' = CH₃
  d X' = F, M' = Na

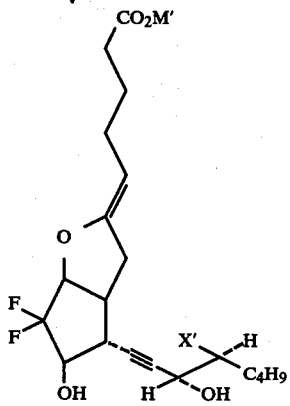

XIVe X' = H, M' = CH₃
  f X' = H, M' = Na
  g X' = F, M' = CH₃
  h X' = F, M' = Na

Diastereomers
XIVa + XIVe
XIVb + XIVf

+

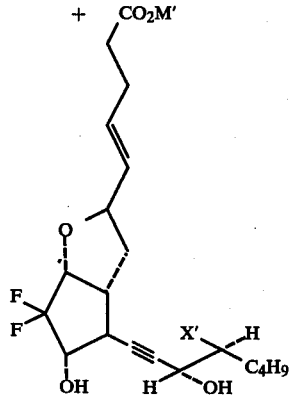

XVa X' = H, M' = CH₃
  b X' = H, M' = Na

+

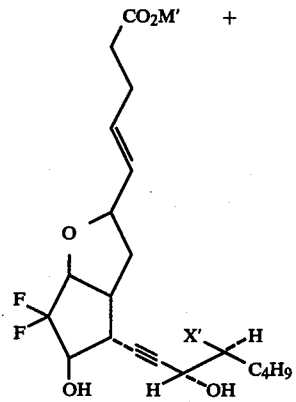

XVe X' = H, M' = CH₃
  f X' = H, M' = Na

Diastereomers
XVa + XVe
XVb + XVf

In the first step of the process of this invention cyclopentane-1,3-dione is converted into the isobutyl ether with isobutanol and a strong acid such as p-toluenesulfonic acid. The resultant racemic enol ether may then be further treated in accordance with this invention with allyl bromide in the presence of a strong base such as lithium diisopropylamide to yield the allyl derivative which is hydrolyzed with a mineral acid such as HCl and the hydrolysis product (IIb) treated with perchloryl fluoride in the presence of potassium bicarbonate. The intermediate difluoro derivative resulting from this reaction is not isolated but immediately reduced with a hydride reducing agent such as potassium tri-sec-butylborohydride to form the difluoro diol (III). This compound is subjected to ozonolysis followed by reductive cleavage of the ozonide, the reducing agent selected being, for example, dimethyl sulfide. The resultant aldehyde, which instantaneously cyclizes to the hemiacetal is not isolated but immediately oxidized with iodine in the presence of sodium carbonate to form the lactone (IV). This lactone may then be dehydrated with trifluoromethanesulfonic anhydride in pyridine at elevated temperature resulting in the unsaturated lactone (V).

At this stage it becomes optional to proceed either with the racemic compound V or to resolve V into its optical antipodes. Whichever course is followed, the reactions themselves and the precise conditions under which they are performed are identical for the whole sequence until the final products of this invention are obtained.

The resolution of the lactone (V) involves hydrolysis of the latter with a base, such as potassium hydroxide, by the reaction of the resultant salt with optically active α-(1-naphthyl)-ethylamine yielding crystalline salts which are recrystallized to constant specific rotation and then treated with a base to decompose the salts and to remove the α-(1-naphthyl)-ethylamine by extraction with ether. The resultant optically active salts are then directly converted into the iodo lactones (VIa) and (VIb) by treatment with iodine and dilute KOH. On the left side of the formula chart set forth above are shown the structures of those enantiomers corresponding in their configuration to the natural prostaglandins. To obtain these enantiomers it is necessary to use (R) (+)-α-(1-naphthyl)-ethylamine. If it is desired to obtain their optical antipodes then (S)(−)-α-(1-naphthyl)-ethylamine must be employed. The resultant iodo lactones may then be carried forward by the process of this invention either in optically active form or as the racemate, which latter alternative is shown in the center of the formula charts. The iodo lactone (VI) are then converted into the epoxy lactones (VII) by treatment with base followed by mild acid treatment. Some of the resultant epoxy acid which fails to lactonize is converted into the methyl ester with diazomethane and then subjected to chromatography on silica gel which causes the methyl ester to lactonize. The epoxy lactones (VII) are then subject to treatment with lithium aluminum hydride at low temperature to form diol epoxides (VIII). These epoxide derivatives are treated with a dialkyl alkynyl aluminum derivative A to form the various acetylenic derivatives (IX) of this invention.

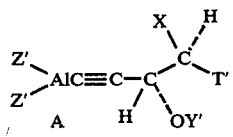

where Z'=lower Alkyl, preferably $CH_3$ or $C_2H_5$; X=H or F; T' is lower alkyl from 3 to 6 carbon atoms, for example butyl or pentyl; and Y' is an alcohol protecting group for example, lower alkyl, such as tert-butyl. The resultant triols IX may then be oxidized with oxygen in the presence of a noble metal catalyst, such as Pt, to form the lactones X. Thus, if in the dialkyl aluminum alkynyl derivatives X is hydrogen, the corresponding triols are formed. If X is fluorine the corresponding fluorinated triols result.

The lactones may then be reduced with a hydride reagent such as diisobutylaluminum hydride at low temperature to form the hemiacetals of this invention XI which, when treated with the ylid prepared from 5-triphenylphosphonio-pentanoic acid yield after removal of the t-butyl protecting group with trifluoroacetic acid the 10,10-difluoro-13-dehydroprostaglandins XII of this invention, which are new products of this invention.

The above prostaglandins of structure XII can then be treated with a diazo-alkane, such as $CH_2N_2$ and the resulting ester derivates cyclized by treatment with a halogen or halogenimide such as iodine and sodium bicarbonate to form the iodo ethers XIII. Treatment with a base, such as for instance diazabicyclo[5,4,0]undec-5-ene results in the formation of the prostacyclins XIV and their $\Delta^4$-isomers XV in the form of their esters which form physiologically active end products of this invention. Additional physiologically active products are formed by hydrolysis of the esters with sodium hydroxide, which gives rise to the corresponding sodium salts XIV and XV, respectively.

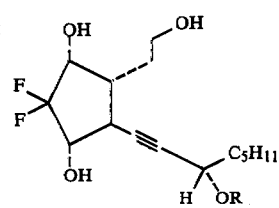

IX(a) R = tBu
(c) R = H

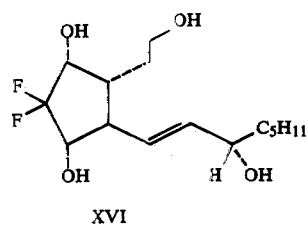

XVI

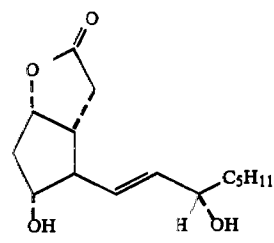

XVII

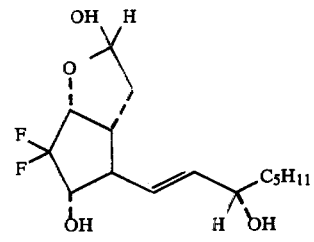

XVIII

-continued

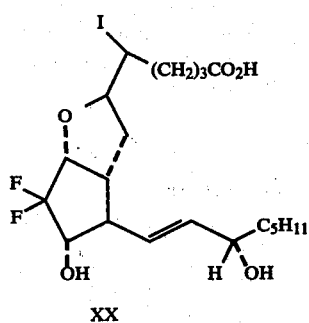

XIX

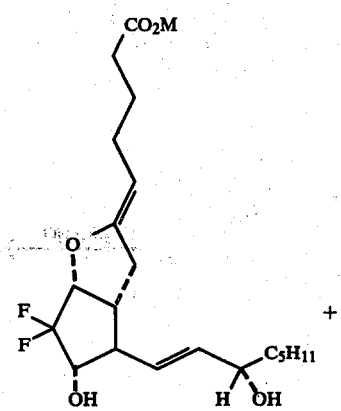

XX

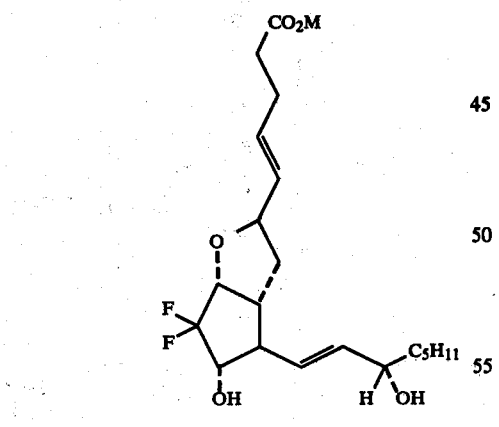

XXI   M = H
XXI(a) M = Na

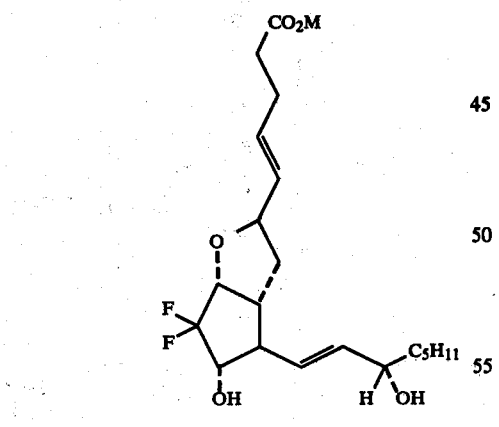

XXII   M = H
XXII(a) M = Na

A further object of this invention is the production of the 10,10-difluoroprostaglandins and the 10,10-difluoroprostacyclins prossessing a trans-double bond in place of the acetylenic bond present in the compounds heretofore described. The synthesis of these compounds starts with the triol-t-butyl ethers IX. Removal of the t-butyl protecting group with trifluoroacetic acid and anisole gives rise to the tetrol IXc, in which the triple bond may now be reduced with lithium aluminum hydride to form the allylic alcohol XVI. Compound XVI may now be treated in the manner hereinbefore described for the sequence of compounds IX to XV, the conditions being very similar to those outlined for the above series of reactions. In this manner there result these additional final pharmacologically active products of this invention XXI and XXII.

The preparation of some of the additional final compounds of this invention entails a number of steps beginning with an unsaturated lactone (Compound 1) as starting material. The steps of the process of this invention may be represented by the following Chart: The values of Y, X, W, T, A, R and M are as hereinbefore defined or otherwise set forth below:

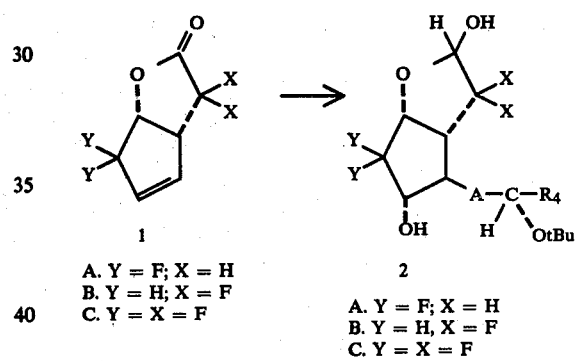

1

A. Y = F; X = H
B. Y = H; X = F
C. Y = X = F

2

A. Y = F; X = H
B. Y = H, X = F
C. Y = X = F

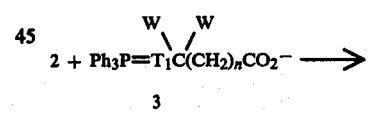

3

A. $T_1$ = CH; W = H
B. $T_1$ = CF; W = F
C. $T_1$ = CF; W = H
D. $T_1$ = CH; W = F

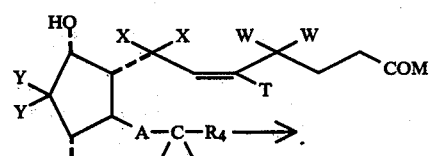

4

A. X = W = F; Y = T = H
B. Y = T = F; X = W = H
C. Y = X = F; T = W = H
D. Y = W = F; T = X = H
E. X = F; Y = W = T = H

-continued

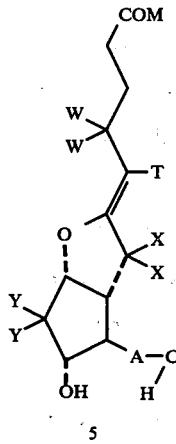

A. X = W = F; Y = T = H
B. Y = T = F; X = W = H
C. Y = X = F; T = W = H
D. Y = W = F; T = X = H
E. X = F; Y = W = T = H

The difluoro-lactones (Compounds 1A may be prepared in accordance with the procedures set forth hereinabove. In order to prepare the tetrafluoro (Compounds 1C) or the difluoro-analogs (Compounds 1B), the following procedure may be employed.

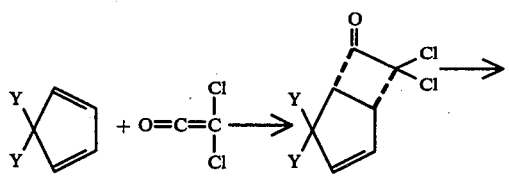

6
A. Y = F
B. Y = H

7
A. Y = F
B. Y = H

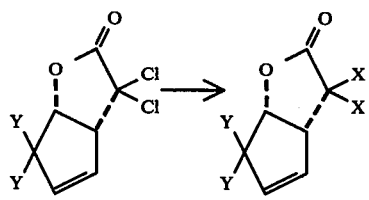

8
A. Y = F
B. Y = H

1

To obtain Compounds 1C or 1B starting materials, the corresponding cyclo-pentadiene (Compounds 6A or 6B) are reacted with a dihalo ketone in accordance with the procedures set forth and taught by L. Ghosez, et al, in Tetrahedron Letters, (1966) page 135, to yield the corresponding Compounds 7. These Compounds 7 may then be further treated in accordance with the teachings of E. J. Corey, et al., Tetrahedron Letters, (1970), page 307, to form the Compounds 8, and then reacted with a fluoride salt, for example, Kf or SbF₃, as described by E. Gryszkilwicz-Trochinowsky, et al, in Rec. Trav. Chim. Pays-Bas, Vol. 66 (1947), page 413, to yield the desired corresponding unsaturated lactone starting materials (Compounds 1).

In addition, the unsaturated lactones (Compounds 1) may also be treated in accordance with the procedures set forth in Fried et al., J. Am. Chem. Soc., 1972, Vol. 94 pp 4342-3 and Fried et al., J. Med. Chem., 1973 Vol. 16, page 429 to yield the corresponding Compounds 2.

Compounds 2 may then be treated in accordance with the procedures set forth herein and treated with a substituted triphenylphosphonioalkanoic acid (Compounds 3) to yield the corresponding prostaglandin (PGF) compounds (Compounds 4).

In order to prepare the required triphenylphosphonioalkanoicacid (Compounds 3) reactants the following procedure may be employed:

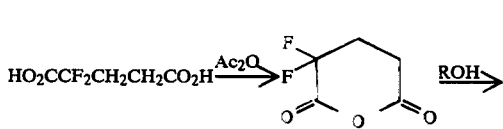

1A     2A

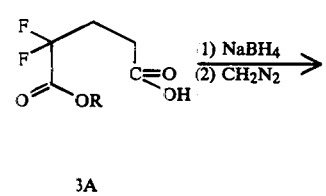

3A

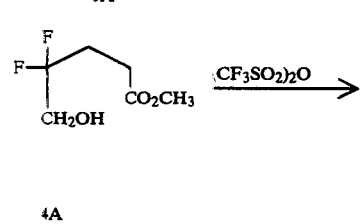

4A

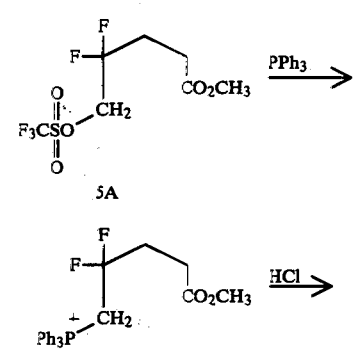

5A

6A

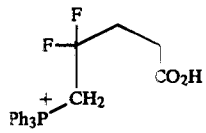

7A

The known difluoro acid 1A will be converted into the anhydride 2A with acetic anhydride and the anhydride opened selectively with an alcohol, e.g., methanol to form the monomethyl ester 3A. The latter will be reduced with a borohydride, e.g., NaBH₄ to the alcohol acid 4A.

Compound 4A may then be treated with $(CF_3SO_2)_2O$ and pyridine to obtain the triflate 5A which can be converted into the triphenylphosphonio derivative with triphenylphosphine. The latter will be hydrolyzed with acid to form the phosphonio acid salts 7A which may be employed for the synthesis of the compounds 4. In addition, the other triphenylphosphonio reactants which are employable in the practice of this invention to yield the 5-fluoro substituted final products, may be prepared in accordance with the following procedure:

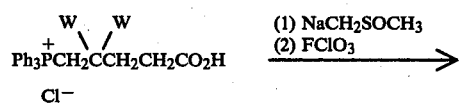

7 A W = F
7 B W = H

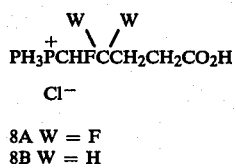

8A W = F
8B W = H

The difluorophosphonio acid 7A or its hydrogen analog 7B is treated with dimsyl sodium and $FClO_3$ to form the corresponding 5-fluoro derivatives, 8A and 8B which may be employed for the synthesis of yet additional compounds 4.

The resultant prostaglandin compounds 4 may then be further treated in accordance with the process of this invention to yield the desired prostacyclin compounds of the invention. Thus, the prostaglandin compounds may be treated as follows:

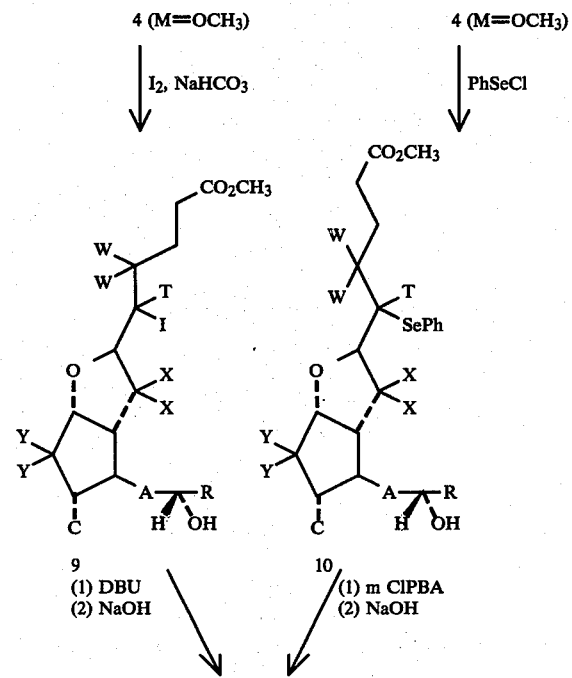

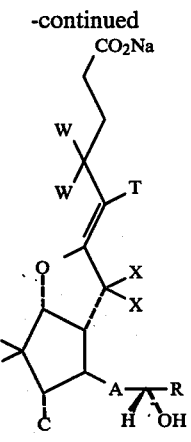

5

Compounds 4 will then be further treated with $I_2$ or an active halogen compound such as N-bromosuccinimide or N-bromodimethylhydantoin to give the compounds 9 usually as a mixture of diaestereomers which will be separated. The major product will be treated with a base, e.g., DBU as detailed herein followed by alkaline hydrolysis to give the end products, the 5-fluoro; 4,4-, 7,7-difluoro; 4,4,5-, 7,7,5- 10,10,5-trifluoro; 4,4,7,7-, 7,7,10,10-, 4,4,10,10-hexafluoro and 4,4,5,7,7,10,10-heptafluoroprostacyclin sodium salts 5.

Compounds 4 will be further treated as described by Nicolaou et al., (J. Am. Chem. Soc., 1978, 100, 2567) as follows: Treatment of 4 with PhSeCl yields compounds 10, which will be oxidized with m-chloroperbenzoic acid to the selenoxides with simultaneous elimination of selenous acid to form after alkaline hydrolysis compounds 5.

In addition to the foregoing, in accordance with the instant invention an alternative process for preparing the prostaglandin (Compounds 4) intermediates of this invention. This alternate method is comprised of a number of steps and may be represented by the following schematic representation:

$EtO_2CCOCH_2CH_2CO_2Et \longrightarrow EtO_2CCF_2CH_2CH_2CO_2Et \longrightarrow$ a                b

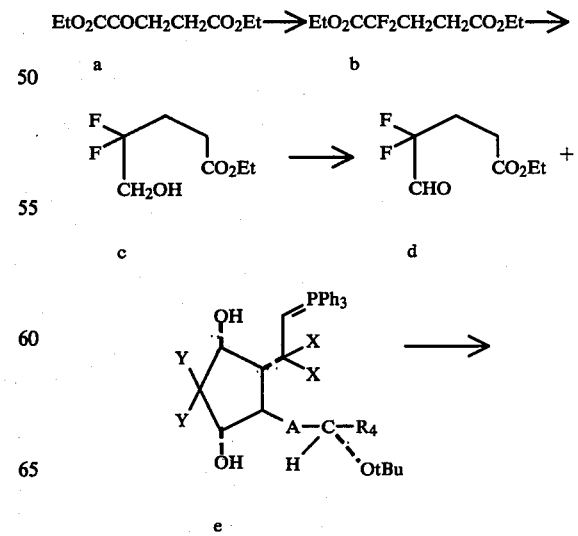

c                d e

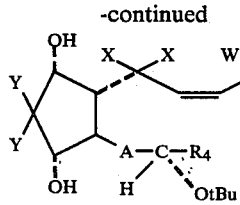

4

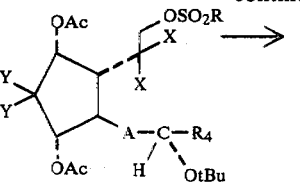

10

In accordance with this alternate procedure, diethyl 2-ketoglutarate (Compound a) is converted into diethyl 2,2-difluoro-glutarate (Compound b) by treatment with $SF_4$ is methylene chloride. Compound b is then selectively reduced with a borohydride, for example, sodium borohydride, to yield the alcohol acid (Compound C), which may then be oxidized, for example, by the Moffatt-Pfitzner method using DMSO-oxalyl chlorie to obtain the aldehyde ester (Compound d). Compound d is then converted into Compounds 4 by treatment with the ylid compound (Compound e) in a Wittig reaction.

The ylid compound (Compound e) which may be employed in the practice of the above described alternate procedure may be prepared in accordance with the following process:

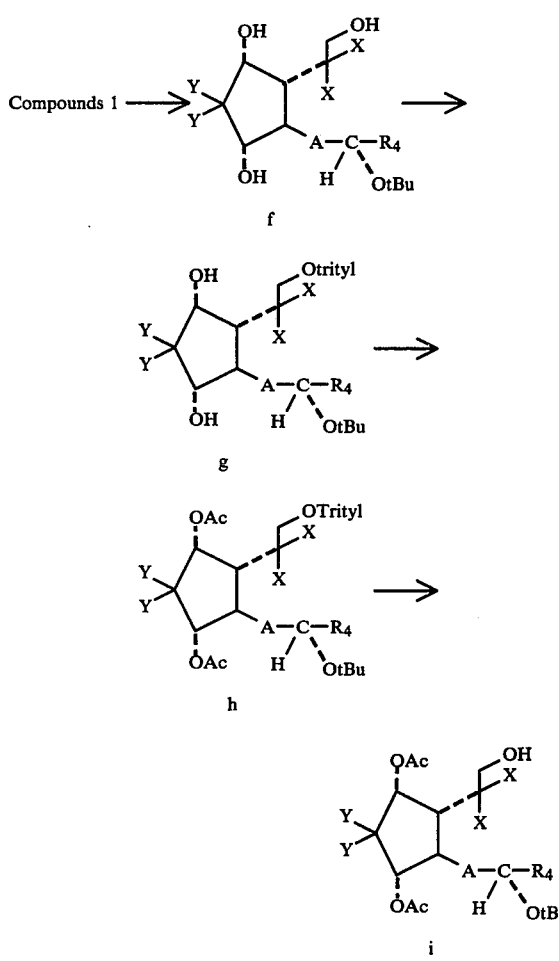

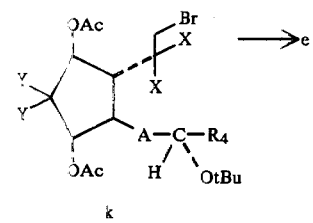

k

Compounds 1 are treated in accordance with the procedures set forth hereinabove in the production of Compounds IXa–IXd, to yield the corresponding polyfluorinated substituted derivatives (Compounds f). Compounds f are then reacted with a triaryl chloromethane, for example, triphenyl chloromethane in pyridine to form the ether Compounds g, which are then treated with an acylating agent, such as, acetic anhydride in pyridine to yield the diester Compounds h. The diesters are then reacted with a dilute organic acid, for example, 90% acetic acid to yield the alcohol Compounds i, which may then be treated with a sulfonating agent, for example, methane sulfonyl chloride in a base, such as pyridine to yield the sulfonated ester Compounds j. These sulfonated Compounds j may then be halogenated by reaction with a metal halide, for example, lithium bromide to yield the corresponding bromide Compounds k. Compounds k may then be treated with a phosphine, such as, triphenyl phosphine to yield the desired acylated phosphonium compounds, which may then be hydrolyzed by treatment with a mild mineral acid, such as hydrochloric acid to yield the corresponding dihydroxy phosphonium compounds, which are then reacted with a strong base, such as butyl lithium to yield the desired ylid compound (Compound e), which may then be employed to obtain the desired prostaglandin compounds (Compounds 4) of this invention, as hereinbefore described.

In addition to the foregoing description, it should be understood that the procedures and practices employed to prepare the compounds of the instant invention are equally applicable to the treatment and processing of other and further intermediate and starting materials to yield further final products which are within the scope of the instant invention. For example, for the many substituents, intermediates or even starting materials which may be available to and employable by the skilled worker in the practice, attention is directed to the following United States Patents, the disclosures of which are incorporated herein by reference: U.S. Pat. Nos. 4,124,599; 4,158,667; 4,174,441; 4,191,824; 4,198,230; 4,198,500; 4,202,970; 4,202,971 and 4,202,972.

Whenever in this specification and the claims appended thereto a wavy line ( ) is employed in the linkage of substituents in the chemical structures set forth, it is meant to denote that the appended moiety may be either in the alpha- or beta- stereochemical configuration in the molecule.

The invention may be further illustrated by the following examples.

The instant invention may be illustrated by the following examples which are to be considered illustrative and not limitative of the instant invention.

EXAMPLE 1

3-Isobutyloxy- $\Delta^2$-cyclopentenone (I)

A solution of B 2.65 g (27 mmole) of cyclopentane-1,3-dione, 25 ml of isobutanol, 30 ml of benzene and 80 mg (0.42 mole) of p-toluenesulfonic acid monohydrate was refluxed under $N_2$ atmosphere in a flask fitted with a Dean Stark water separator. After 1 hr 20 min the mixture was cooled and most of the benzene and isobutanol was evaporated under reduced pressure. The residue was poured into 40 ml of water containing 160 mg of $Na_2CO_3$ and extracted with 60 ml (40+20 ml) of benzene. The benzene layer was washed with 20 ml of water, separated, dried over anhydrous $Na_2SO_4$ and finally evaporated to give 4.01 g (96.3%) of 3-isobutyloxy-$\Delta^2$-cyclopentenone (I) which was used in the subsequent reaction without further purification. The compound solidifies in the refrigerator and remelts at room temperature. Boiling point 112° at 3 mm.

Anal. Calcd for $C_9H_{14}O_2$: C, 65.74; H, 5.86. Found: C, 65.58; H, 5.77

EXAMPLE 2

3-Isobutyloxy-5-allyl-$\Delta^2$-cyclopentenone (IIa)

n-BuLi (2.2 ml, 4.84 mmole) was added to a well stirred solution of 1.3 ml of diisopropylamine in 20 ml of tetrahydrofuran at $-20°$ under $N_2$ atmosphere. After 5 min, the clear solution was cooled to $-78°$ and to this was added a solution of 613 mg (3.98 mmole) of 3-isobutyloxy-$\Delta^2$-cyclopentenone (I) in 24 ml of tetrahydrofuran. The addition was done over 2.5 min and the resulting solution was pale yellow. After a further 15 min at $-78°$, 1 ml of allyl bromide was added. The mixture was then allowed to warm up to $-25°$ over a period of 20 min and quenched with 5 ml of water. The organic solvents were evaporated and the residual aqueous layer was extracted with 15 ml of benzene. The benzene layer was dried over anhydrous $Na_2SO_4$, concentrated and finally distilled at 0.16 mm (outside oil bath temperature 75°-85°) to give 615 mg (79.6%) of 3-isobutyloxy-5-allyl-$\Delta^2$-cyclopentenone (IIa). A further 26 mg (3.4%) of somewhat impure (IIa) was collected as a higher boiling fraction (80° at 0.1 mm).

Anal. Calcd for $C_{12}H_{18}O_2$: C, 74.22; H, 9.27. Found: C, 73.94; H, 9.18.

EXAMPLE 3

4-allylcyclopentane-1,3-dione (IIb)

A homogeneous solution of 1.835 g (9.46 mmole) of 3-isobutyloxy-5-allyl-$\Delta^2$-cyclopentenone (IIa) in 85 ml of tetrahydrofuran and 60 ml of 1 N HCl was heated at 52° (outside oil bath temperature) for 2 hrs. It was then cooled and the organic solvent was evaporated under reduced pressure. The turbid residue was diluted with water to a total volume of 100 ml and extracted with 10 ml of benzene. The remaining aqueous layer was reextracted with 250 ml (100+100+50 ml) of ethyl acetate. The ethyl acetate layer was dried and evaporated to give 1.173 g (89.9%) of 4-allylcyclopentane-1,3-dione (IIb). In an attempt to crystalline the compound from 1:1 ethyl acetate:hexane only an oil was obtained, which later solidified on standing. Melting point of this solid 50.5°–60.5°.

Anal. Calcd for $C_8H_{10}O_2$: C, 69.56; H, 7.25. Found: C, 69.77; H, 7.51.

EXAMPLE 4

All-cis-1,1-difluoro-2,5-dihydroxy-3-allyl-cyclopentane (III)

A stream of $PClO_3$, purified by passing successively through 2 N NaOH solution, 5% $Na_2S_2O_3$ solution and methanol was bubbled at 20° through a solution of 2 g (14.5 mole) of 4-allycyclopentane-1,3-dione (IIb) in 360 ml of methanol containing 3.19 g (31.9 mole) of $KHCO_3$ until the reaction mixture was neutral. The reaction proceeds with formation of a white precipitate of $KClO_3$. Excess $PClO_3$ was removed by bubbling $N_2$ through the mixture. Toluene (50 ml) was added and the methanol was evaporated under reduced pressure. An additional 50 ml of toluene was added and the mixture was cooled to $-40°$ under $N_2$. K-Selectride (220 ml of 0.5 M solution in THF) was added over a 10 min period while maintaining the temperature at $-40°$ to $-78°$. After a further 20 min, 37 ml of 3 M NaOH solution was added followed by 45 ml of 30% $H_2O_2$, the latter being added over a 20 min period at $-10°$. The reaction mixture was then saturated with solid NaCl and extracted with 800 ml (650+150 ml) of benzene. The organic layer was washed successively with 15 ml of 3 M NaOH, 15 ml of 4 N HCl, 10 ml of saturated NaCl and 10 ml of 3 M NaOH. The organic layer was then dried and evaporated. The residue was placed on 50 g silica gel and the column washed with 500 ml of benzene, which completely eluted the compound added as stabilizer to tetrahydrofuran. The column was then washed with a further 1 liter portion of benzene containing 10% ethyl acetate and the solvents evaporated in vacuo. The residue was rechromatographed on 350 g of silica gel. The column was washed with 4.5 liter of benzene containing 2.5% ethyl acetate. It was then eluted with 7 l of benzene containing 2.5% acetate. It was then eluted with 7 l of benzene containing 5% ethyl acetate and 880 fractions of equal volume were collected. Fractions 211 through 450 contained 940 mg (36.4%) of all-cis-1,1-difluoro-2,5-dihydroxy-3-allylcyclopentane (III).

Anal. Calcd for $C_8H_{12}F_2O_2$. C, 53.93; H, 6.74; F. 21.34. Found: C, 54.12; H, 6.68; F, 20.98.

EXAMPLE 5

All cis-1,1-difluoro-2,5-dihydroxy-3-carboxymethylcyclopentane 2,2'-Lactone (IV)

A stream of ozone was bubbled through a solution of 900 mg (5.06 mmole) of all cis-1,1-difluoro-2,5-dihydroxy-3-allylcyclopentane (III) in 100 ml of methanol at $-70°$ until the mixture was pale blue. Excess $O_3$ was blown out by $N_2$ and the intermediate hydroperoxide was decomposed by dimethylsulfide first at $-70°$ and then at room temperature overnight. All the solvents were evaporated and the crude product was kept in high vacuum for a few days until it solidified. Nmr of this crude product shows it to be essentially pure hemiacetal. The crude hemiacetal obtained obove was then dissolved in 12 ml of water containing 1 g KI. Solid $I_2$ (2.5634 g, 10.10 mmole) and a solution of 4.14 g (39 mmole) of $Na_2 CO_3$ in 9 ml of water were alternately added in small and approximately equal portions over a period of 30 min. After an additional 10 min, excess $I_2$ was reduced by adding $Na_2SO_3$, and HCl was added to make the solution distinctly acidic. The aqueous layer was then extracted with 400 ml (200+100+100 ml) of ethyl acetate, and the organic layer washed with 15 ml (10+5 ml) of water containing little $Na_2SO_3$ and KI. The ethyl acetate layer was dried over anhydrous $Na_2SO_4$, evaporated and finally azeotroped with benzene for 1½ hrs in a flask fitted with a Dean Stark water separator. All the benzene was evaporated and the crude residue was chromatographed on 100 g of silica gel. The column was eluted with 1 l of 25% ethyl acetate/75% benzene and 500 ml of 50% ethyl acetate/50% benzene and 180 fractions of equal volume were collected. Fractions 59 through 110 contained 660 mg (73.3%) of all cis-1,-difluoro-2,5-dihydroxy-3-carboxymethylcyclopentane 2,2'-lactone (IV) (crystallized from chloroform mp 76.5°–77.5°).

Anal. Calcd for $C_7H_8F_2O_3$. C, 47.19; H, 4.49; F, 21.34. Found: C, 47.15; H, 4.66; F, 20.91.

EXAMPLE 6

1,1-Difluoro-2,3-cis-2-hydroxy-3-carboxymethyl-$\Delta^4$-cyclopentene-2,2'-Lactone (V)

Trifluoromethanesulfonic anhydride (0.825 ml, 4.09 mmole) was added through a syringe over a period of 3–4 min, to a solution of 610 mg (3.43 mmole) of all cis-1,1-difluoro-2,5-dihydroxy-3-carboxymethylcyclopentane 2,2'-lactone (IV) in 3 ml of pyridine at $-10°$. The mixture was brought to room temperature and most of the pyridine was evaporated by a stream of $N_2$. The last trace of pyridine was evaporated with 8 ml of benzene and the residue was extracted with 24 ml (3×8 ml) of benzene. The benzene extract was evaporated and the crude triflate was taken up in 4 ml of pyridine and refluxed for 12 min. The mixture was cooled and poured into 20 ml of 4 N HCl and extracted with 160 ml (2×80 ml) of benzene. The benzene layer was washed with 10 ml of water, dried and evaporated. The residue was chromatographed over 60 g of silica gel pretreated with benzene containing 1% pyridine. The column was eluted with 2 l of benzene containing 0.5% pyridine and 250 equal volume fractions were collected. Fractions 81–140 contained 418 mg (76.2%) of 1,1-difluoro-2,3-cis-2-hydroxy-3-carboxymethyl-$\Delta^4$-cyclopentene 2,2'-lactone (V) (mp 36°–37°).

Anal. Calcd for $C_7H_6F_2O_2$. C, 52.50; H, 3.75; F, 23.75. Found: C, 52.88; H, 4.01; F, 23.52.

EXAMPLE 7

1,1-Difluoro-2,4-cis-dihydroxy-2,3-cis-3-carboxymethyl-2,5-trans-5-iodocyclopentane 4,2'-Lactone (VI)

A solution of 40 mg (0.25 mmole) of 1,1-difluoro-2,3-cis-hydroxy-3-carboxy-$\Delta^4$-cyclopentene 2,2'-lactone (V) in 1 ml of 0.5 N methanolic KOH was stirred overnight. Excess KOH was then buffered by bubbling $CO_2$ through the solution and methanol (8 ml) and 1.874 g (7.4 mmole)$I_2$ was added. After a further 5 hrs at room temperature 25 ml of ethyl acetate was added and the reaction mixture was evaporated to dryness. The residue was dissolved in 50 ml of ethyl acetate and washed with 25 ml (15+10 ml) of water containing $Na_2SO_3$. The organic layer was then dried over anhydrous $Na_2SO_4$ and evaporated to give 1,1-difluoro-2,4-cis-dihydroxy-2,3-cis-3-carboxymethyl-2,5-trans-5-iodocyclopentane-4,2'-lactone (VI) in essentially quantitative yield. (Crystallized from chloroform mp 118°–119.5°.

Anal. Calcd for $C_7H_7F_2IO$ g. C, 27.63; H, 2.30; F, 12.50; I, 41.77. Found: C, 27.53; H, 2.40; F, 12.94; I, 42.19.

EXAMPLE 8

(2R,3R,4S,5R)-1,1-Difluoro-2,4-dihydroxy-3-carboxymethyl-5-iodocyclopentane 4,2'-Lactone (VIa)

A solution of the olefinic lactone racemate V (160 mg, 1.0 mmole) in 0.1 M KOH/MeOH (16 ml, 1.6 mmole) was stirred at room temperature for 16 hrs. Methanol was evaporated ($N_2$) and the salt dissolved in water (3 ml). Ethyl acetate (10 ml) was added and the mixture cooled with stirring to 0°. 10% Oxalic acid was added dropwise to lower the pH to 2. The ethyl acetate layer was separated and the aqueous layer extracted with ethyl acetate (2×10 ml). The combined ethyl acetate layers were dried ($MgSO_4$) and (R)-(+)-$\alpha$-(1-naphthyl) ethylamine (200 µl. 2.0 mg, 1.23 mmole) was added. After 16 hrs at room temperature, the precipitated solid was separated after centrifugation. Crystallization from ethyl acetate (23–25 ml) at 70% gave a crystalline salt (135.1 mg. 38.7%). Melting point 161°–162°.

$[\alpha]_{CH_3OH}^D = -45.34$ (c, 1.48).

This salt (40 mg, 0.11 mmole) was dissolved in 0.1M NaOH (5 ml, 0.5 mmole) and the aqueous solution extracted with ether (3×6 ml) to remove the free amine. The basic aqueous solution was acidified to pH 1 with concentrated HCl and extracted with ether (4×6 ml). The combined ether extracts were dried ($MgSO_4$) and evaporated, and the residue was dissolved in 0.1M KOH/MeOH (4 ml, 0.4 mmole) and stirred at room temperature (24°) for 3 hrs. Pieces of dry ice were added to lower the pH to 8–9, followed by solid iodine in one portion (400 mg, 1.57 mmole, 14 fold excess). The contents were stirred at room temperature (24°) for 14 hours in the dark, the methanol evaporated ($N_2$), ethyl acetate (2 ml) added and evaporated ($N_2$). The residue was dissolved in ethyl acetate (8 ml) and washed successively with saturated $Na_2SO_3$, water and brine. Removal of ethyl acetate after drying ($MgSO_4$) gave the iodolactone VIa as a sticky solid (34.9 mg, quantitative). The crude product was crystallized from $CHCl_3$ (0.7–0.8 ml) at 60° to give colorless crystals (15.5 mg, 44.5%). Melting point: 157°–158°. $[\alpha]_D^{25} = +76.03$ (c, 0.63, $CH_3OH$).

EXAMPLE 9

(2S,3S,4R,5S)-1,1-Difluoro-2,4-dihydroxy-3-carboxymethyl-5-iodocyclopentane-4,2'-Lactone(VIb)

Following the procedure of Example 8 but substituting (s)-(−)-$\alpha$-(naphthyl)ethylamine for the (+)-enantiomer there is obtained the title compound (VIb).

EXAMPLE 10

All cis-1,1-difluoro-2-hydroxy-3-carboxymethyl-4,5-epoxycyclopentane 2,2'-Lactone (VIIa)+(VIIb)

A solution of 29.6 mg (0.13 mmole) of 1,1-difluoro-2,4-cis-dihydroxy-2,3-cis-3-carboxymethyl-2,5-trans-5-iodocyclopentane 4,2'-lactone, (VI) in 4 ml of 1N methanolic KOH was stirred at room temperature for 20 hrs. Excess KOH was buffered by $CO_2$. The mixture was concentrated to 2 ml, 8 ml of benzene was added, and all the solvents were evaporated. The residue was taken up in 0.5 ml of water at 0° and acidified with 0.5N $HClO_4$ to pH 2. The aqueous solution was extracted with 70 ml (40+30 ml) of ethyl acetate, the ethyl acetate layer treated with diazomethane and evaporated. The residue was taken up in chloroform, separated from insoluble matter and evaporated to give 29.5 mg of crude compound which is mostly all cis-1,1-difluoro-2-hydroxy-3-carboxymethyl-4,5-epoxycyclopentane methyl ester. This compound was dissolved in little benzene and poured on to 9 g silica gel. After 20 hrs the column was eluted with 100 ml of benzene. Elution with further 200 ml of benzene containing 5% ethyl acetate gave, after evaporation of the solvents, 16.9 mg (73.7% of racemic all cis-1,1-difluoro-2-hydroxy-3-carboxymethyl-4,5-epoxycyclopentane 2,2'-lactone (VIIa)+(VIIb). Crystallization from chloroform-hexane gave 12 mg (52.3%) of the pure title compound. Mp 91.5°–92.5°.

Anal. Calcd for $C_7H_6F_2O_3$. C, 47.72; H, 3.41; F, 21.59. Found: C, 47.96; H, 3.45; F, 21.24

EXAMPLE 11

(2R,3R,4S,5S)-1,1-Difluoro-2-hydroxy-3-carboxymethyl-4,5-epoxycyclopentane-2,2'-Lactones (VIIa)

Following the procedure of Example 10 but substituting the enantiomer VIa for the racemate VIa+VIb there is obtained the title compound (VIIa). Mp 110°–11°; $[\alpha]_D^{CHCl_3} - 113°$.

EXAMPLE 12

(2S,3S,4R,5R)-1,1-Difluoro-2-hydroxy-3-carboxymethyl-4,5-epoxycyclopentane 2,2'-Lactone (VIIb)

Following the procedure of Example 10 but substituting the enantiomer VIb for the racemate there is obtained the title compound (VIIb). Mp 110.5°–111°; $[\alpha]_D^{CHCl_3} - 102.4°$.

EXAMPLE 13

All cis-1,1-Difluoro-2-hydroxy-3[2'-hydroxyethyl]-4,5-epoxycyclopentane (VIIIa)+(VIIIb).

To a suspension of LiAlH$_4$ in THF (2.5 ml) at $-40°$ was added within 2 min. a solution of the racemic lactone-epoxide (VIIa)+(VIIb) in THF (2.0 ml), under N$_2$ and the reaction mixture stirred at this temperature for 3 hrs. The reaction was quenched by the dropwise addition of saturated Na K tartrate (1.5 ml). The suspension was extracted with EtOAc, dried (Na$_2$SO$_4$) and evaporated to dryness. The crude reaction product was purified by tlc. [CHCl$_3$:MeOH 9:1] to give the pure title compound (VIIIa)+(VIIIb) 109.2 mg (86.59%). It was crystallized from ether hexane; mp 50°–50.5°.

EXAMPLE 14

(2R,3R,4S,5S)-1,1-Difluoro-2-hydroxy-3[2'-hydroxyethyl]-4,5-epoxycyclopentane (VIIIa).

Following the procedure of Example 13 but substituting the [2S,3S,4R,5R-lactone VIIa for the racemate there is obtained the title compound (VIIIa). Mp 59°–59.5°; $[\alpha]_D^{25} - 23°$(CHCl$_3$).

EXAMPLE 15

(2S,3S,4R,5R)-1,1-Difluoro-2-hydroxy-3[2'-hydroxyethyl]-4,5-epoxycyclopentane (VIIIb)

Following the procedure of Example 13 but substituting the (2R,3R,4S,5R)-lactone VIIb for the racemate there is obtained the title compound (VIIIb). Mp 58°–59°; $[\alpha]_D^{25} +23.1°$ (CHCl$_3$).

EXAMPLE 16

(15S)-1,2,3,4,5-Pentanor-6,9,11,15-tetrahydroxy-10,10-difluoro-13-prostyne 15-tert butyl ether (IXa)+(IXc)

To (3S)-t-butyloxy-1-octyne (225 mg) was added at 0° 2.7N n-BuLi (435 µl) over a course of 1 min and the reaction mixture stirred at this temperature for 6 min. To the solution was added dimethylchloroalane (680 µl) over a 30 second period and the reaction mixture stirred at 0° for 50 min. To the above reagent consisting of dimethyl-(3S)-t-butyloxy-1-octynylalane was added a solution of the racemic epoxydiol (VIIIa)+(VIIIb) (10.0 mg) in dry toluene (0.85 ml) and the reaction mixture allowed to warm up slowly to room temperature. The reaction vessel was then immersed in a preheated oil bath (55°) and the reaction mixture held at this temperature for 6 hrs. After cooling to 0° a saturated solution of Na$_2$SO$_4$ was added dropwise, until no more effervescence occurred, and the mixture filtered through a sintered glass funnel. The Al salts were washed repeatedly with ether, until colorless. The filtrate was transferred to a separatory funnel and the two layers separated. The aqueous layer was extracted again with ether. The combined ether extracts were washed with brine, dried (Na$_2$SO$_4$) and evaporated to yield the crude reaction product as a yellow oil. Tlc showed the presence of some unreacted epoxydiol. The crude reaction product was purified by column chromatography. The title compound IXa+IXc was eluted with EtOAc:-hexane (4:6).

EXAMPLE 17

(8R,9P,11S,12S,15S)-1,2,3,4,5-Pentanor-6,9,11,15-tetrahydroxy-10,10-difluoro-13-prostynel-15-tert-butyl ether (IXa)

Following the procedure of Example 16 but substituting the diol epoxide VIIIa for the racemate there is obtained the title compound (IXa). $[\alpha]_D^{25} -45.3°$ (CHCl$_3$).

EXAMPLE 18

(8S,9S,11R,12R,15S)-1,2,3,4,5-Pentanor-6,9,11,15-tetrahydroxy-10,10-difluoro-13-prostyne-15-tert-butyl ether (IXc)

Following the procedure of Example 16 but substituting the diol epoxide VIIIb for the racemate there is obtained the title compound (IXc). $[\alpha]_D^{25} +29.5°$ (CHCL$_3$).

EXAMPLE 19

(8R,9R,11S,12S,15S,16S)-1,2,3,4,5-Pentanor-6,9,11,15-tetrahydroxy-10,10-16-trifluoro-13-prostyne-15-tert-butyl ether (IXb)

Following the procedure of Example 17 but substituting dimethyl-3-t-butyloxy-4-fluoro-1-octynylalane for the dimethyl-3-t-butyloxy-1-octynylalane there is obtained the title compound (IXb).

EXAMPLE 20

(8S,9S,11R,12R,15S,16S)-1,2,3,4,5-Pentanor-6,9,11,15-tetrahydroxy-10,10,16-trifluoro-13-prostyne-15-tert-butyl ether (IXd)

Following the procedure of Example 19 but substituting the epoxydiol VIIIb for its antipode VIIIa there is obtained the title compound (IXd).

EXAMPLE 21

(15S)-1,2,3,4,5-Pentanor-9,11,15-trihydroxy-10,10-difluoro-13-prostyn-6-oic acid 6,9-lactone 15-tert butyl ether (Xa)+(Xc).

PtO$_2$ (60 mg) and 9.0 ml of H$_2$O were placed in a 50 ml 3-necked round bottom flask fitted with two stoppers and a gas inlet adapter. The system was evacuated and then filled with H$_2$ (3 times) and the catalyst stirred in a H$_2$ atmosphere for 15 min. The system was evacuated, filled with N$_2$ and the 3-necked flask fitted with a condenser and a rubber septum with a needle through which O$_2$ could be bubbled into the reaction mixture. The triol IXa+IXc (56.0 mg) in 10.2 ml of aqueous acetone [acetone:H$_2$ 1:4] was injected into the reaction vessel. The triol did not dissolve completely in the above solvent system. The test tube containing the triol was therefore rinsed with an additional 6 ml of acetone and this solution was also added. Into the reaction mixture was bubbled O$_2$ with stirring and heating at 58° for 5 hrs. It was then passed through a pad of celite (15 g), and washed repeatedly with EtOAc. The aqueous layer was separated and concentrated in vacuum to 6–7 ml, saturated with NaCl and extracted again with EtOAc. The combined EtOAc extracts were washed with brine, dried (Na$_2$SO$_4$) and evaporated to yield the crude title compound Xa+Xc as a yellow gum. It was purified by tlc, and yielded 41.7 mg of pure reaction product, (75%).

EXAMPLE 22

(8R,9R,11S,12S,15S)1,2,3,4,5-Pentanor-9,11,15-trihydroxy-10,10-difluoro-13-prostyn-6-oic acid 6,9-lactone 15-tert butyl ether (Xa).

Following the procedure of Example 21 but substituting the triol IXa for the diastereomers IXa+IXc there is obtained the title compound (Xa). $[\alpha]_D^{25} - 50.5°$ (CHCl$_3$).

EXAMPLE 23

(8S,9S,11R,12R,15S)-1,2,3,4,5-Pentanor-9,11,15-trihydroxy-10,10-difluoro-13-prostyn-6-oic acid 6,9-lactone 15-tert butyl ether (Xc)

Following the procedure of Example 21 but substituting the triol IXc for IXa+IXc there is obtained the title compound (Xc). $[\alpha]_D^{25} - 30.3°$ (CHCl$_3$).

EXAMPLE 24

(8R,9R,11S,12S,15S,16S)-1,2,3,4,5-Pentanor-9,11,15-trihydroxy-10,10,16-trifluoro-13-prostyn-6-oic acid 6,9-lactone 15-tert butyl ether (Xb)

Following the procedure of Example 21 but substituting the trifluoro triol IXb for the triol IXa+IXc there is obtained the title compound (Xb).

EXAMPLE 25

(8S,9S,11R,12R,15S,16S)-1,2,3,4,5-Pentanor-9,11,15-trihydroxy-10,10,16-trifluoro-13-prostyn-6-oic acid 6,9-lactone 15-tert butyl ether (Xd)

Following the procedure of Example 21 but substituting the trifluoro triol IXd for the triol IXa+IXd there is obtained the title compound (Xd).

EXAMPLE 26

(15S)-1,2,3,4,5-Pentanor-9,11,15-trihydroxy-10,10-difluoro-13-prostyn-6-al hemiacetal 15-tert butyl ether (XIa)+(XIc)

Diisobutyl aluminum hydride (141 μl) was added dropwise to a stirred solution of 29.4 mg of the lactone Xa+Xc in 0.45 ml of toluene at −70° over a 30 second period and the reaction mixture stirred at this temperature for 1 hr. To the mixture was added dropwise a saturated Na$_2$SO$_4$ solution. It was then extracted repeatedly with ether, the ether extract washed with brine, dried (Na$_2$SO$_4$) and evaporated to yield 30 mg of the crude title compound (XIa)+(XIc). Purification of tlc yielded 268 mg of the pure hemiacetal (90.66%).

EXAMPLE 27

(8R,9R,11S,12S,15S)-1,2,3,4,5-Pentanor-9,11,15-trihydroxy-10,10-difluoro-13-prostyn-6-al hemiacetal 15-tert butyl ether (XIa)

Following the procedure of Example 26 but substituting the lactone Xa for the lactone Xa+Xc there is obtained the title compound (XIa). $[\alpha]_D^{25} - 56.5°$ (CHCl$_3$).

EXAMPLE 28

(8S,9S,11R,12R,15S)-1,2,3,4,5-Pentanor-9,11,15-trihydroxy-10,10-difluoro-13-prostyn-6-al hemiacetal 15-tert butyl ether (XIc)

Following the procedure of Example 26 but substituting the lactone Xc for the lactone Xa+Xc there is obtained the title compound (XIc). $[\alpha]_D^{25} - 39.0$ (CHCl$_3$).

EXAMPLE 29

(8R,9R,11S,12S,15S,16S)-1,2,3,4,5-Pentanor-9,11,15-trihydroxy-10,10,16-trifluoro-13-prostyn-6-al hemiacetal 15-tert butyl ether (XIb)

Following the procedure of Example 26 but substituting the lactone Xb for the lactone Xa+Xc there is obtained the title compound (XIb).

EXAMPLE 30

(8S,9S,11R,12R,15S,16S)-1,2,3,4,5-Pentanor-9,11,15-trihydroxy-10,10,16-trifluoro-13-prostyn-6-al hemiacetal 15-tert butyl ether (XId)

Following the procedure of Example 26 but substituting the lactone Xd for the lactone Xa+Xc there is obtained the title compound (XId).

EXAMPLE 31

10,10-Difluoro-13-dehydroprostaglandin F$_{2\alpha}$ tert butyl ether (XIIa)+(XIIg)

NaH (159 mg, 50% oil dispersion) was placed in a centrifuge tube, the tube evacuated, flushed with N$_2$ (3 times) and 3.30 ml of dimethylsulfoxide was injected. The tube was then immersed in a preheated oil bath at 70° (ca. 69°–72°) and held at this temperature, for ca. 1 hr, with stirring. The mixture was cooled to room temperature and centrifuged. To this dimsyl sodium solution was added dropwise at 25° 5-triphenylphosphonio-n-pentanoic acid bromide (189.0 mg) dissolved in 526 μl of DMSO. After 480 μl had been added and the red color persisted an additional 384 μl of dimsyl sodium was added and the resulting solution stirred at 25° for 10 min. The hemiacetal (25.0 mg) in 150 μl of DMSO was injected into the above solution of the ylide at 25°, followed by two rinsings of a total of 40 μl. The reaction mixture was then allowed to stir at room temperature for 1 hr, following which it was cooled in ice water and acidified with N/10 HCl, to a pH of 1. It was then extracted repeatedly with EtOAc and the EtOAc extract washed with brine, dried (Na$_2$SO$_4$) and evaporated to dryness to yield 196 mg of a pale yellow viscous liquid. This material was triturated with 8 ml of Et$_2$O-EtOAc (2:1), which caused most of the phosphonio salt to precipitate. It was centrifuged off, the solid washed repeatedly with ether and the mother liquor and ether washings concentrated to dryness. The residue was triturated again with 3 ml of Et$_2$O-EtOAc 1:1 and was allowed to remain at −20° overnight, when 20.0 mg more of the above salt precipitated. It was centrifuged, the solid washed repeatedly with Et$_2$O and the mother liquor and ether washings concentrated to dryness to yield 45.2 mg of the title compound (XIIa)+(XIIg) as a light brown oil. This oil was purified by tlc. The pure reaction product amounted to 23.9 mg (77%).

EXAMPLE 32

10,10-Difluoro-13-dehydroprostaglandin F$_{2\alpha}$ 15-tert butyl ether (XIIa)

Following the procedure of Example 31 but substituting the isomer XIa for the mixture of XIa+XIc there is obtained the title compound (XIIa).

EXAMPLE 33

10,10-Difluoro-13 -dehydroprostaglandin F$_{2\alpha}$ 15-tert butyl ether (XIIg)

Following the procedure of Example 31 but substituting the isomer XIc for the mixture of XIa+XIc there is obtained the title compound (XIIg).

EXAMPLE 34

10,10,16-Trifluoro-13-dehydroprostaglandin F$_{2\alpha}$ 15-tert butyl ether (XIIb)

Following the procedure of Example 31 but substituting the trifluorohemiacetal XIb for the difluorohemiacetal XIa+XIc there is obtained the title compound (XIIb).

EXAMPLE 35

10,10,16-Trifluoro-13-dehydroprostaglandin F$_{2\alpha}$ tert butyl ether (XIIh)

Following the procedure of Example 31 but substituting the trifluorohemiacetal XId for the difluorohemiacetal XIa+XIc there is obtained the title compound (XIIh).

EXAMPLE 36

10,10-Difluoro-13-dehydroprostaglandin F$_{2\alpha}$ (XIIc+XIIi)

To 23.5 mg of the t-butyloxy compound XIIa+XIIg was added at 0° 300 μl of ice cold trifluoroacetic acid and 10 μl of anisole and the reaction mixture stirred at 0° for 2 hrs. At the end of this period, 2 ml of CCl$_4$ was added and the mixture blown down with N$_2$. This process was repeated several times and the resulting product was dried in vacuum for 0.5 hr. It was then stirred with 1 ml of a solution of saturated Na$_2$CO$_3$ and 1 ml of H$_2$O for 1 hr, at the end of which period the solution was extracted with Et$_2$O. The Na$_2$CO$_3$ layer was acidified with cold 10% HCl to pH 1 and extracted repeatedly with EtOAc. The EtOAc extract was washed with brine, dried, (Na$_2$SO$_4$) and evaporated to yield 18.2 mg of a yellow gum, which was purified by tlc. The weight of pure 10,10-difluoro-13-dehydro-PGF$_{2\alpha}$ XIIc+XIIi was 17.3 mg (84.36%).

EXAMPLE 37

10,10-Difluoro-13-dehydroprostaglandin F$_{2\alpha}$ (XIIc)

Following the procedure of Example 36 but substituting compound XIIa for the mixture of XIIa+XIIg there is obtained the title compound (XIIc). $[\alpha]_D^{25}$ +28.7° (MeOH).

EXAMPLE 38

10,10-Difluoro-13-dehydroprostaglandin F$_{2\alpha}$ (XIIi)

Following the procedure of Example 36 but substituting compound MIIg for the mixture of XIIa+XIIg there is obtained the title compound (XIIi). $[\alpha]_D^{25}$ −21.3° (MeOH).

EXAMPLE 39

10,10-Difluoro-13-dehydroprostaglandin F$_{2\alpha}$ (XIId)

Following the procedure of Example 36 but substituting the trifluoro compound XIIb for the difluoro mixture of XIIa+XIIg there is obtained the title compound ((XIId).

EXAMPLE 40

10,10-Difluoro-13-dehydroprostaglandin F$_{2\alpha}$ (XIIj)

Following the procedure of Example 36 but substituting the trifluoro compound XIIh for the difluoro mixture of XIIa+XIIg there is obtained the title compound (XIIj).

EXAMPLE 41

10,10-Difluoro-5-iodo-9-deoxy-6,9-oxido-13-dehydroprostaglandin F$_{1\alpha}$ Methyl ester (XIIIa)+(XIIIx)

10,10-Difluoro-13-dehydro-PGF$_{2\alpha}$XIIc+XIIi (5.3 mg) in 3 ml of Et$_2$O-MeOH 2:1 was treated at 0° with CH$_2$N$_2$ in ether until the yellow color persisted. After 5 min. at 0° dilute AcOH (AcOH-Et$_2$O 1:1) was added until the yellow color disappeared. The solvents were blown down with a stream of N$_2$ and the residue subjected to high vacuum for 0.5 hr. The weight of the methyl ester XIIe+XIIk was 5.5 mg. The above methyl ester was added to saturated NaHCO$_3$ (2.0 ml) and a 2.5% solution of I$_2$ in ether (0.80 ml) and the mixture stirred at 0° for 1 hr. A dilute aqueous solution of sodium thiosulfate was added to the reaction mixture dropwise until it became colorless. It was then extracted repeatedly with ether. The ether extract was washed with brine, dried (Na$_2$SO$_4$) and evaporated to yield the crude title compound XIVa+XIIIc as a light yellow oil, which was purified by tlc. The weight of the pure iodo compound was 5.8 mg (81%).

EXAMPLE 42

10,10-Difluoro-5-iodo-9-deoxy-6,9-oxido-13-dehydroprostaglandin F$_{1\alpha}$ Methyl ester (XIIIa)

Following the procedure of Example 41 but substituting the compound XIIc for XIIc+XIIi there is obtained the title compound (XIIIa).

EXAMPLE 43

10,10-Difluoro-5-iodo-9-deoxy-6,9-oxido-13-dehydroprostaglandin $F_{1\alpha}$ Methyl ester (XIIIc)

Following the procedure of Example 41 but substituting the compound XIIi for XIIc+XIIi there is obtained the title compound (XIIIc).

EXAMPLE 44

10,10,16-Trifluoro-5-iodo-9-deoxy-6,9-oxido-13-dehydroprostaglandin $F_{1\alpha}$ Methyl ester (XIIIb)

Following the procedure of Example 41 but substituting the trifluoro compound XIId for the difluoro compound XIIc+XIIi there is obtained the title compound (XIIIb).

EXAMPLE 45

10,10,16-Trifluoro-5-iodo-9-deoxy-6,9-oxido-13-dehydroprostaglandin $F_{1\alpha}$ Methyl ester (XIIId)

Following the procedure of Example 41 but substituting the trifluoro compound XIIj for the difluoro compound XIIIc+XIIi there is obtained the title compound (XIIId).

EXAMPLE 46

10,10-Difluoro-13-dehydro prostacyclin Methyl ester (XIVa)+(XIVe) and its $\Delta^4$-Isomer (XVA)+(XVe)

A solution of 3.9 mg of the iodo compound XIIIa+XIIIc in 200 μl of toluene was degassed and flushed with $N_2$. 1,5-Diaza[5,4,0]bicycloundec-5-ene (DBU, 6.7 μl) was then syringed into the reaction vessel, which was immersed into a preheated oil bath at 90°. The reaction mixture was allowed to cool to room temperature and diluted with 0.5 ml of hexane:EtOAc (4:1). The precipitated solid was filtered through glass wool and the reaction vessel washed three times with the same solvent. The combined washings were cooled to 0° and washed with an equally cold pH 7 buffer and then with ice-cold distilled water. The organic extracts were dried quickly over $MgSO_4$-$K_2CO_3$ (1:1 W.W) and evaporated to yield 3.2 mg of the crude reaction product. The components present in the crude reaction product were separated by tlc (acetone-methylene chloride 3:7). 10,10-Difluoro-13-dehydroprostacyclin methyl ester moved slightly faster than its $\Delta^4$-isomer. The separated fractions were rechromatographed yielding the pure difluorodehydroprostacyclin methyl ester XIVa+XIVe 1.4 mg. The following slower moving fraction (1.6 mg) was rechromatographed and yielded the pure $\Delta^4$-derivative XVa+XVe, 0.5 mg.

EXAMPLE 47

10,10-Difluoro-13-dehydro prostacyclin Methyl ester (XIVa) and its $\Delta^4$-Isomer (XVa)

Following the procedure of Example 46 but substituting the iodo compound XIIIa for the mixture XIIIa+XIIIc there are obtained the title compounds (XIVa) $[\alpha]_D^{25}$+45° (MeOH) and (XVa).

EXAMPLE 48

10,10-Difluoro-13-dehydroprostacyclin Methyl ester (XIVe) and its $\Delta^4$Isomer (XVe)

Following the procedure of Example 46 but substituting the iodo compound XIIIc for the mixture XIIIa+XIIIc there are obtained the title compounds (XIVe) $[\alpha]$−2.8° (MeOH) and (XVe).

EXAMPLE 49

10,10,16-Trifluoro-13-dehydroprostacyclin Methyl ester (XIVc) and its $\Delta^4$-Isomer (XVc)

Following the procedure of Example 46 but substituting the trifluoro-iodo compound XIIIb for the mixture XIIIa+XIIIc there are obtained the title compounds (XIVc) and (XVc).

EXAMPLE 50

10,10,16-Trifluoro-13-dehydroprostacyclin Methyl ester (XIVg) and its $\Delta^4$-Isomer (XVg)

Following the procedure of Example 46 but substituting the trifluoro-iodo compound XIIId for the mixture XIIIa+XIIIc there are obtained the title compounds (XIVg) and (XVg).

EXAMPLE 51

10,10-Difluoro-13-dehydroprostacyclin sodium salt (XIVb)+(XIVf)

10,10-Difluoro-13-dehydroprostacyclin methyl ester (1.4 mg) in 0.2 ml of MeOH was stirred with 0.5N NaOH (0.70 ml), at room temperature for 2 hrs. Dry ice was then added to bring the pH of the solution down to 9. Most of the MeOH and water were blown down with $N_2$ and the residual gum was subjected to high vacuum for 18 hrs. The solid residue consisting of 10,10-difluoroprostacyclin sodium salt XIVb and $Na_2CO_3$ (for stabilization) is stored in the freezer.

EXAMPLE 52

10,10-Difluoro-13-dehydroprostacyclin sodium salt (XIVb)

Following the procedure of Example 51 but substituting the methyl ester XIVa for the mixture XIVa+XIVe there is obtained the title compound (XIVb).

EXAMPLE 53

10,10-Difluoro-13-dehydroprostacyclin sodium salt (XIVf)

Following the procedure of Example 51 but substituting the methyl ester XIVe for the mixture XIVa+XIVe there is obtained the title compound (XIVf).

EXAMPLE 54

10,10,16-Trifluoro-13-dehydroprostacyclin sodium salt (XIVd)

Following the procedure of Example 46 but substituting the trifluoro methyl ester XIVe for the difluoro ester mixture XIVa+XIVe there is obtained the title compound (XIVd).

EXAMPLE 55

10,10,16-Trifluoro-13-dehydroprostacyclin sodium salt (XIVh)

Following the procedure of Example 46 but substituting the trifluoro ester XIVg for the mixture XIVa+XIVe there is obtained the title compound (XIVh).

EXAMPLE 56

10,10-Difluor-13-dehydroprostacyclin (4E)-Isomer Sodium Salt (XVb)+(XVf)

Following the procedure of Example 46 but substituting the methyl ester XVa+XVe for the mixture XIVa+XIVe there is obtained the title compound (XVb)+(XVf).

EXAMPLE 57

10,10-Difluoro-13-dehydroprostacyclin (4E)-Isomer Sodium Salt (XVb)

Following the procedure of Example 46 but substituting the methyl ester XVa for the mixture XIVa+XIVe there is obtained the title compound (XVb).

EXAMPLE 58

10,10-Difluoro-13-dehydroprostacyclin (4E)-Isomer Sodium Salt (XVf)

Following the procedure of Example 46 but substituting the methyl ester XVe for the mixture XIVa+XIVe there is obtained the title compound (XVf).

EXAMPLE 59

10,10,16Trifluoro-13-dehydroprostacyclin (4E)-Isomer (XVd)

Following the procedure of Example 46 but substituting the trifluoro methyl ester XVc for the mixture XIVa+XIVe there is obtained the title compound (Xvd).

EXAMPLE 60

10,10,16-Trifluoro-13-dehydroprostacyclin (4E)-Isomer (XVh)

Following the procedure of Example 46 but substituting the trifluoro methyl ester XV for the mixture XIVa+XIVe for the racemate there is obtained the title compound (XVh)

EXAMPLE 61

(8R,9R,11S,15S)-1,2,3,4,5-Pentanor-6,9,11,15tetrahydroxy-10,10-difluoro-13-prostyne (IXc)

Trifluoroacetic acid (2.50 ml) was added in one portion to 146 mg of the t-butyl-triol-yne (IXa) cooled to 0°-5°. The magnetically stirred solution was placed in a cold room at −15°, and the reaction followed by tlc. After completion (4 hr), workup of the reaction was performed at 0°-5° with addition of saturated $Na_2CO_3$ solution (approx. 17 ml) until pH 10 followed by addition of 13 ml of MeOH. The contents were stirred at room temperature of 0.5 hr, 10% HCl was added until the solution was neutral followed by addition of 50 ml of saturated NaCl solution. The aqueous solution was extracted with $CHCl_3$ (10×50 ml), the combined $CHCl_3$ extracts washed with saturated NaCl solution (2×250 ml), and the $CHCl_3$ layer dried over anhydrous $Na_2SO_4$. Filtration and evaporation of the solvent under vacuum gave 120 mg (100%) of the tetraol-yne (IXc) which showed a single component via tlc (ir indicated the absence of any sodium trifluoroacetate and esters of trifluoroacetic acid).

EXAMPLE 62

(8R,9R,11S,15S)-1,2,3,4,5-Pentanor-6,9,11,15-tetrahydroxy-10,10-difluoro-13-prostene (XVI)

Lithium aluminum hydride (0.148 g, 4.10 mmole) the tetraol-yne IXc (45 mg, 0.15 mmole) and 1.5 ml of dry THF were placed in a round bottom flask fitted with a spiral reflux condenser and drying true. The contents were heated at gentle reflux in an oil bath maintained at 70°, and the reaction followed by glc. After 4 hrs, the reaction vessel was cooled to 0°-5° and 10% HCl was added until the evolution of gas ceased followed by addition of 30 ml of saturated NaCl solution. The aqueous solution was extracted with EtOAc (8×50 ml) the EtOAc extracts washed with saturated NaCl solution (1×), and then dried over anhydrous $Na_2SO_4$. Filtration and removal of solvent under vacuum gave 40 mg (88%) of crude material.

Column chromatography of the above isolated material with silica gel using EtOAc and EtOAc-MeOH (10:1) as the eluents gave 32 mg (80%) of the pure tetraol-ene XVI as a slightly colored yellow oil.

EXAMPLE 63

(8R,9R,11S,12S)-1,2,3,4,5-Pentanor-9,11,15-trihydroxy-10,10-difluoro-13-prosten-6-oic acid 6,9-lactone (XVII)

Following the procedure of Example 21 but substituting the tetrol-ene XVI for the triol-yne IXa+IXc there is obtained the title compound (XVII).

EXAMPLE 64

(8R,9R,11S,12S,15S)-1,2,3,4,5-Pentanor-9,11,15-trihydroxy-10,10-difluoro-13-prostyn-6-al hemiacetal (XVIII)

Following the procedure of Example 26 but substituting the ene lactone XVII for the yne lactone Xa+Xc there is obtained the title compound XVIII.

EXAMPLE 65

10,10-Difluoroprostaglandin $F_{2\alpha}$ (XIX)

Following the procedure of Example 36 but substituting the ene hemiacetal XVIII for the yne hemiacetal XIa+XIc there is obtained the title compound (XIX).

EXAMPLE 66

10,10-Difluoro-5-iodo-9-deoxy-6,9-oxidoprostaglandin $F_{1\alpha}$ (XX)

Following the procedure of Example 41 but substituting 10,10-difluoro $PGF_{2\alpha}$ for its 13-dehydro derivative XIIIa+XIIIc there is obtained the title compound (XX).

EXAMPLE 67

10,10-Difluoroprostacyclin Methyl ester (XXI) and its $\Delta^4$-Isomer (XXII)

Following the procedure of Example 46 but substituting the ene iodo compound XX for the yne iodo compound XIIIa+XIIIc there are obtained the title compounds (XXI) and (XXII).

EXAMPLE 68

10,10-Difluoroprostacyclin (XXIIa)

Following the procedure of Example 51 but substituting 10,10-difluoro-prostacyclin methyl ester XXII for the 13-dehydro methyl ester XIVa+XIVe there is obtained the title compound (XXIa).

EXAMPLE 69

Following the procedure set forth in Example 16, but substituting equivalent amounts of either dimethyl-3-t-butyloxy-1-nonynylalene, or dimethyl-3-t-butyloxy-4-fluoro-1-nonynylalene for the dimethyl-3-t-butyloxy-1-octynylalene the corresponding homologous derivatives are obtained.

EXAMPLE 70

2,2-Difluoroglutaric Anhydride

A solution of 5 g of 2,2-difluoroglutaric acid in 20 ml of acetic anhydride is refluxed for two hrs, 5 ml of the resulting solution is distilled off at ordinary pressure and the residual solution freed from acetic anhydride under reduced pressure. The resulting oil consists of 2,2-difluoroglutaric anhydride.

EXAMPLE 71

2,2-Difluoroglutaric acid 1-Methyl Ester

A solution of 3 g of 2,2-difluoroglutaric anhydride in 25 ml of dry methanol is allowed to remain at 25° for 18 hrs. At the end of this period the methanol is removed in vacuo leaving behind 2,2-difluoroglutaric 1-methyl ester as an oil.

EXAMPLE 72

4,4-Difluoro-5-hydroxy-n-pentanoic Acid Methyl Ester

To a solution of 2 g of 2,2-difluoroglutaric acid 1-methyl ester in 20 ml of methanol is added at 25° 250 mg of sodium borohydride and the mixture allowed to remain at 25° for 2 hrs. The solution is diluted with water and acidified to pH 1 with 1N HCl and the methanol removed in vacuo. The residual suspension is extracted with methylene chloride and the extract dried with sodium sulfate and evaporated to dryness in vacuo. The residual oil is treated with ethereal diazomethane until the yellow color persists and the ether is removed in vacuo. There remains behind the title compound.

EXAMPLE 73

4,4-Difluoro-5-triphenylphosphoniopentanoic Acid Hydrochloride

A solution of 1.68 g of 4,4-difluoro-5-hydroxy-n-pentanoic acid methyl ester and 3.10 g of trifluoromethylsulfonic anhydride (1.1 equ.) in 10 ml of dry pyridine is allowed to remain at 25° for 18 hrs. The mixture is taken up in ether, extracted with ice-cold water, 1N HCl and again with water and the ether extract evaporated to dryness in vacuo. The residual triflate is treated with 2.9 g of triphenylphosphine in 30 ml of acetonitrile at 25° for 24 hrs and the mixture diluted with an equal volume of 1.5n HCl. After heating to reflux for 1 hr the solution is cooled and the acetonitrile and hydrochloric acid removed in vacuo. The residue is triturated with benzene upon which it solidifies to yield the title compound.

EXAMPLE 74

5-Fluoro-5-triphenylphosphoniopentanoic Acid

To a solution of dimsyl sodium in 5 ml of dimethylsulfoxide prepared from 84 mg of sodium hydride is added 888 mg of 5-triphenylphosphoniopentanoic acid hydrochloride in 15 ml of DMSO. Into this solution is bubbled at 25° purified perchlorylfluoride until the solution is neutral. Water is then added and dilute HCl and the fluoroacid extracted with methylene chloride. The organic extract is dried over sodium sulfate and evaporated to dryness in vacuo leaving behind the fluoroacid.

EXAMPLE 75

4,4,5-Trifluoro-5-triphenylphosphoniopentanoic Acid

Following the procedure of Example 74 but substituting an equivalent amount of 4,4-difluoro-5-triphenylphosphoniopentanoic acid hydrochloride in the reaction there is obtained the title compound.

EXAMPLE 76

1,1-Difluoro-2,3-cis-2-hydroxy-3-carboxydifluoromethyl-$\Delta^4$-cyclopentene 2,2'-lactone 1(C)

A solution of 500 mg of 1,1-difluoro-2,3-cis-2-hydroxy-3-carboxydichloromethyl-$\Delta^4$-cyclopentene 2,2'-lactone prepared from 1,1-difluoro cyclopentadiene and dichloroketene according to Ghosez et al., Tetrahedron Lett., 1966, page 135 and Corey et al., Tetrahedron Lett. 1970, page 307, and 1.0 g of anhydrous potassium fluoride in 15 ml of anhydrous diethylene glycol is heated at 110° for 18 hrs. The mixture is cooled, diluted with water and extracted with ethyl acetate. The ethyl acetate extract is washed with water, dried over sodium sulfate and evaporated to dryness in vacuo, leaving the title compound as an oil.

EXAMPLE 77

2,3-cis-2-Hydroxy-3-Carboxydifluoromethyl-$\Delta^4$-cyclopentene 2,2'-Lactone

Following the procedure of Example 76 but substituting an equivalent amount of 2,3-cis-2-hydroxy-3-carboxydifluoromethyl-$\Delta^4$-cyclopentene 2,2'-lactone in the reaction there is obtained the title compound.

EXAMPLE 78

1,1-Difluoro-2,4-cis-dihydroxy-2,3-cis-3-carboxydifluoromethyl-2,5-trans-5-iodocyclopentane 4,2'-Lactone A solution of 40 mg of 1,1-difluoro-2,3-cis-hydroxy-3-carboxydifluoromethyl-$\Delta^4$-cyclopentene 2,2'-lactone in 1 ml of 0.5N methanolic KOH was stirred overnight. Excess KOH was then buffered by bubbling $CO_2$ through the solution and methanol (8 ml) and 1.874 g of $I_2$ was added. After a further 5 hrs at room temperature 25 ml of ethyl acetate was added and the reaction mixture was evaporated to dryness. The residue was dissolved in 50 ml of ethyl acetate and washed with 25 ml (15+10 ml) of water containing $Na_2SO_3$. The organic layer was then dried over anhydrous $Na_2SO_4$ and evaporated to give 1,1-difluoro-2,4-cis-dihydroxy-2,3-cis-3-carboxydifluoromethyl-2,5-trans-5-iodocyclopentane 4,2'-lactone in essentially quantitative yield.

EXAMPLE 79

2,4-cis-Dihydroxy-2,3-cis-3-carboxydifluoromethyl-2,5-trans-5-iodocyclopentane 4,2'-lactone Following the procedure of Example 78 but substituting an equivalent amount of 2,3-cis-2-hydroxy-3-carboxydifluoromethyl-$\Delta^4$-cyclopentene 2,2'-lactone in the reaction there is obtained the title compound.

EXAMPLE 80

All cis-1,1-difluoro-2-hydroxy-3-carboxydifluoromethyl-4,5-epoxycyclopentane 2,2'-Lactone A solution of 29.6 mg of 1,1-difluoro-2,4-cis-dihydroxy-2,3-cis-3-carboxydifluoromethyl-2,5-trans-5-iodocyclopentane 4,2'-lactone in 4 ml of 1N methanolic KOH was stirred at room temperature for 20 hrs. Excess KOH was buffered by $CO_2$. The mixture was concentrated to 2 ml, 8 ml of benzene was added, and all the solvents were evaporated. The residue was taken up in 0.5 ml of water at 0° and acidified with 0.5N $HClO_4$ to pH 2. The aqueous solution was extracted with 70 ml (40+30 ml) of ethyl acetate, the ethyl acetate layer treated with diazomethane and evaporated. The residue was taken up in chloroform, separated from insoluble matter and evaporated to give 29.5 mg of crude compound which is mostly all cis-1,1-difluoro-2-hydroxy-3-carboxydifluoromethyl-4,5-epoxycyclopentane methyl ester. This compound was dissolved in little benzene and poured on to 9 g silica gel. After 20 hrs the column was eluted with 100 ml of benzene. Elution with further 200 ml of benzene containing 5% ethyl acetate gave, after evaporation of the solvents, 16.9 mg of all cis-1,1-difluoro-2-hydroxy-3-carboxydifluoromethyl-4,5-epoxycyclopentane 2,2'-lactone.

EXAMPLE 81

All cis-2-Hydroxy-3-carboxydifluoromethyl-4,5-epoxycyclopentane 2,2'-Lactone Following the procedure of Example 80 but substituting an equivalent amount of the iodolactone of Example 79 there is obtained the title compound.

EXAMPLE 82

All cis-1,1-Difluoro-2-hydroxy-3[2'-hydroxy-1'-difluoroethyl]-4,5-epoxycyclopentane To a suspension of $LiAlH_4$ in THF (2.5 ml) at −40° was added within 2 min a solution of the lactoneepoxide of Example 11 in THF (2.0 ml) under $N_2$ and the reaction mixture stirred at this temperature for 3 hrs. The reaction was quenched by the dropwise addition of saturated Na K tartrate (1.5 ml). The suspension was extracted with EtOAc, dried $Na_2SO_4$) and evaporated to dryness. The crude reaction product was purified by tlc. [$CHCl_3$:MeOH 9:1] to give the pure title compound 109.2 mg (86.59%).

EXAMPLE 83

All cis-2-Hydroxy-3[2'-hydroxy-1'-difluoroethyl]-4,5-epoxycyclopentane

Following the procedure of Example 82 but substituting an equivalent amount of the lactone epoxide of Example 81 in the reaction there is obtained the title compound.

EXAMPLE 84

(15S)-1,2,3,4,5-Pentanor-6,9,11,15-tetrahydroxy-7,7,10,10-tetrafluoro-13-prostyne 15-tert-butyl ether To (3S)-t-butyloxy-1-octyne (225 mg) was added at 0° 2.7N n-BuLi (435 μl) over a course of 1 min and the reaction mixture stirred at this temperature for 6 min. To the solution was added dimethylchloroalane (680 μl) over a 30 second period and the reaction mixture stirred at 0° for 50 min. To the above reagent consisting of dimethyl-(3S)-t-butyloxy-1-octynylalene was added a solution of the racemic epoxydiol of Example 82 (10.0 mg) in dry toluene (0.85 ml) and the reaction mixture allowed to warm up slowly to room temperature. The reaction vessel was then immersed in a preheated oil bath (55°) and the reaction mixture held at this temperature for 6 hrs. After cooling to 0° a saturated solution of $Na_2SO_4$ was added dropwise, until no more effervescence occurred, and the mixture filtered through a sintered glass funnel. The aluminum salts were washed repeatedly with ether, until colorless. The filtrate was transferred to a separatory funnel and the two layers separated. The aqueous layer was extracted again with ether. The combined ether extracts were washed with brine, dried ($Na_2SO_4$) and evaporated to yield the crude reaction product as a yellow oil. Tlc showed the presence of some unreacted epoxydiol. The crude reaction product was purified by column chromatography. The title compound was eluted with EtOAc:benzene (4:6).

EXAMPLE 85

(15S)-1,2,3,4,5-Pentanor-6,9,11,15-tetrahydroxy-7,7-difluoro-13-prostyne 15-tert-butyl ether Following the procedure of Example 84 but substituting an equivalent amount of the diol epoxide of Example 83 in the reaction there is obtained the title compound.

EXAMPLE 86

(15S)-1,2,3,4,5-Pentanor-9,11,15-trihydroxy-7,7,10,10-tetrafluoro-13-prostyn-6-oic acid 6,9-lactone 15-tert butyl ether $PtO_2$ (60 mg) and 9.0 ml of $H_2O$ were placed in a 50 ml 3-necked round bottom flask fitted with two stoppers and a gas inlet adapter. The system was evacuated and then filled with $H_2$ (3 times) and the catalyst stirred in a $H_2$ atmosphere for 15 min. The system was evacuated, filled with $N_2$ and the 3-necked flask fitted with a condenser and a rubber septum with a needle through which $O_2$ could be bubbled into the reaction mixture. The triol of Example 15 (56.0 mg) in 10.2 ml of aqueous acetone [acetone:$H_2$ 1:4] was injected into the reaction vessel. The triol did not dissolve completely in the above solvent system. The test tube containing the triol was therefore rinsed with an additional 6 ml of acetone and this solution was also added. Into the reaction mixture was bubbled $O_2$ with stirring and heating at 58° for 5 hrs. It was then passed through a pad of celite (15 g), and washed repeatedly with EtOAc. The aqueous layer was separated and concentrated in vacuum to 6–7 ml, saturated with NaCl and extracted again with EtOAc. The combined EtOAc extracts were washed with brine, dried ($Na_2SO_4$) and evaporated to yield the crude title compound as a yellow gum. It was purified by tlc, and yielded 41.7 mg of pure reaction product.

EXAMPLE 87

(15S)-1,2,3,4,5-Pentanor-9,11,15-trihydroxy-7,7-difluoro-13-prostyn-6-oic acid 6,9-lactone 15-tert-butyl ether Following the procedure of Example 86 but substituting an equivalent amount of the triol of Example 85 in the reaction there is obtained the title compound.

EXAMPLE 88

(15S)-1,2,3,4,5-Pentanor-9,11,15-trihydroxy-7,7,10,10-tetrafluoro-13-prostyn-6-al hemiacetal 15-tert-butyl ether Diisobutyl aluminum hydride (141 μl) was added dropwise to a stirred solution of 29.4 mg of the lactone of Example 86 in 0.45 mg of toluene at −70° over a 30 second period and the reaction mixture stirred at this temperature for 1 hr. To the mixture was added dropwise a saturated $Na_2SO_4$ solution. It was then extracted repeatedly with ether, the ether extract washed with brine, dried ($Na_2SO_4$) and evaporated to yield 30 mg of the crude title compound. Purification by tlc yielded 26.8 mg of the pure hemiacetal (90.66%).

EXAMPLE 89

(15S)-1,2,3,4,5-Pentanor-9,11,15-trihydroxy-7,7-difluoro-13-prostyn-6-al hemiacetal 15-tert-butyl ether Following the procedure of Example 88 but substituting an equivalent amount of the lactone of Example 87 in the reaction there is obtained the title compound.

EXAMPLE 90

7,7,10,10-Tetrafluoro-13-dehydroprostaglandin $F_{2\alpha}$ tert-butyl ether

NaH (159 mg, 50% oil dispersion) was placed in a centrifuge tube, the tube evacuated, flushed with $N_2$ (3 times), and 3.30 ml of dimethylsulfoxide was injected. The tube was then immersed in a preheated oil bath at 70° (ca. 69°–72°) and held at this temperature, for ca. 1 hr, with stirring. The mixture was cooled to room temperature and centrifuged. To this dimsyl sodium solution was added dropwise at 25° 5-triphenylphosphonio-n-pentanoic acid (189.0 mg) dissolved in 526 μl of DMSO. After 480 μl had been added and the red color persisted an additional 384 μl of dimsyl sodium was added and the resulting solution stirred at 25° for 10 min. The hemiacetal (25.0 mg) of Example 88 in 150 μl of DMSO was injected into the above solution of the ylide at 25°, followed by two rinsings of a total of 40 μl. The reaction mixture was then allowed to stir at room temperature for 1 hr, following which it was cooled in ice water and acidified with N/10 HCl, to a pH of 1. It was then extracted repeatedly with EtOAc and the EtOAc extract washed with brine, dried ($Na_2SO_4$) and evaporated to dryness to yield 196 mg of a pale yellow viscous liquid. This material was triturated with 8 ml of $Et_2O$-$EtOAc$ (2:1), which caused most of the phosphonio salt to precipitate. It was centrifuged off, the solid washed repeatedly with ether and the mother liquor and ether washings concentrated to dryness. The residue was triturated again with 3 ml of $Et_2O$-EtOAc 1:1 and was allowed to remain at −20° overnight, when 20.0 mg more of the above salt precipitated. It was centrifuged, the solid washed repeatedly with $Et_2O$ and the mother liquor and ether washings concentrated to dryness to yield 45.2 mg of the title compound as a light brown oil. This oil was purified by tlc. The pure reaction product amounted to 23.9 mg (77%).

EXAMPLE 91

7,7-Difluoro-13-dehydroprostaglandin $F_{2\alpha}$ 15-tert-butyl ether

Following the procedure of Example 90 but substituting an equivalent amount of the hemiacetal of Example 89 in the reaction there is obtained the title compound.

EXAMPLE 92

4,4,7,7-Tetrafluoro-13-dehydroprostaglandin $F_{2\alpha}$ 15-tert-butyl ether

Following the procedure of Example 91 but substituting an equivalent amount of 4,4-difluoro-5-triphenylphosphoniopentanoic acid hydrochloride there is obtained the title compound.

EXAMPLE 93

4,4,10,10-Tetrafluoro-13-dehydroprostaglandin $F_{2\alpha}$ 15-tert-butyl ether

Following the procedure of Example 92 but substituting an equivalent amount of the 10,10-difluorohemiacetal for the 7,7,10,10-tetrafluorohemiacetal there is obtained the title compound.

EXAMPLE 94

5,10,10-Trifluoro-13-dehydroprostaglandin $F_{2\alpha}$ 15-tert-butyl ether

Following the procedure of Example 93 but substituting an equivalent amount of the 5-fluoro-5-triphenylphosphoniopentanoic acid for the 4,4-difluoro acid there is obtained the title compound.

EXAMPLE 95

7,7,10,10-Tetrafluoro-13-dehydroprostaglandin $F_{2\alpha}$

To 23.5 mg of the t-butyloxy compound of Example 90 was added at 0° 300 μl of ice cold trifluoroacetic acid and 10 μl of anisole and the reaction mixture stirred at 0° for 2 hrs. At the end of this period, 2 ml of $CCl_4$ was added and the mixture blown down with $N_2$. This process was repeated several times and the resulting product was dried in vacuum for 0.5 hr. It was then stirred with 1 ml of a solution of saturated $Na_2CO_3$ and 1 ml of $H_2O$ for 1 hr, at the end of which period the solution was extracted with $Et_2O$. The $Na_2CO_3$ was acidified with cold 10% HCl to pH 1 and extracted repeatedly with EtOAc. The EtOAc extract was washed with brine, dried, ($Na_2SO_4$) and evaporated to yield 18.2 mg of a yellow gum, which was purified by tlc. The weight of pure 7,7,10,10-tetrafluoro-13-dehydro-$PGF_{2\alpha}$ was 17.3 mg.

EXAMPLE 96

7,7-Difluoro-13-dehydroprostaglandin $F_{2\alpha}$

Following the procedure of Example 95 but substituting an equivalent amount of 7,7-difluoro t-butyl ether of Example 91 for the 7,7,10,10-tetra-fluoro derivative there is obtained the title compound.

EXAMPLE 97

4,4,7,7-Tetrafluoro-13-dehydroprostaglandin $F_{2\alpha}$

Following the procedure of Example 95 but substituting an equivalent amount of 4,4,7,7-tetrafluoro t-butyl ether of Example 92 there is obtained the title compound.

EXAMPLE 98

4,4,10,10-Tetrafluoro-13-dehydroprostaglandin $F_{2\alpha}$

Following the procedure of Example 95 but substituting an equivalent amount of 4,4,10,10-tetrafluoro t-butyl ether of Example 93 there is obtained the title compound.

EXAMPLE 99

5,10,10-Trifluoro-13-dehydroprostaglandin $F_{2\alpha}$

Following the procedure of Example 95 but substituting an equivalent amount of the 5,10,10-tetrafluoro compound of Example 94 there is obtained the title compound.

EXAMPLE 100

7,7,10,10-Tetrafluoro-5-iodo-9-deoxy-6,9-oxido-13-dehydroprostaglandin $F_{1\alpha}$ Methyl ester A solution of 7,7,10,10-Tetrafluoro-13-dehydro-$PG_{2\alpha}$ (5.3 mg) in 3 ml of $Et_2O$-MeOH 2:1 was treated at 0° with $CH_2N_2$ in ether until the yellow color persisted. After 5 min at 0° dilute AcOH (AcOH-$Et_2O$ 1:1) was added until the yellow color disappeared. The solvents were blown down with a stream of $N_2$ and the residue subjected to high vacuum for 0.5 hr. The weight of the methyl ester was 5.5 mg. The above methyl ester was added to saturated $NaHCO_3$ (2.0 ml) and a 2.5% solution of $I_2$ in ether (0.80 ml) and the mixture stirred at 0° for 1 hr. A dilute aqueous solution of sodium thiosulfate was added to the reaction mixture dropwise until it became colorless. It was then extracted repeatedly with ether. The ether extract was washed with brine, dried ($Na_2SO_4$) and evaporated to yield the crude title compound as a light yellow oil, which was purified by tlc. The weight of the pure iodo compound was 5.8 mg (81%).

EXAMPLE 101

7,7-Difluoro-5-iodo-9-deoxy-6,9-oxido-13-dehydro-prostaglandin $F_{1\alpha}$ Methyl ester Following the procedure of Example 100 but substituting an equivalent amount of the 7,7-difluoro compound of Example 96 there is obtained the title compound.

EXAMPLE 102

4,4,7,7-Tetrafluoro-5-iodo-9-deoxy-6,9-oxido-13-dehydroprostaglandin $F_{1\alpha}$ Methyl ester Following the procedure of Example 100 but substituting an equivalent amount of the 4,4,7,7 compound of Example 97 there is obtained the title compound.

EXAMPLE 103

4,4,10,10-Tetrafluoro-5-iodo-9-deoxy-6,9-oxido-13-dehydroprostaglandin $F_{1\alpha}$ Methyl ester Following the procedure of Example 100 but substituting an equivalent amount of the 4,4,10,10 compound of Example 98 there is obtained the title compound.

EXAMPLE 104

5,10,10-Tetrafluoro-5-iodo-9-deoxy-6,9-oxido-13-dehydroprostaglandin $F_{1\alpha}$ Methyl ester Following the procedure of Example 100 but substituting an equivalent amount of the 5,10,10-trifluoro compound of Example 99 there is obtained the title compound.

EXAMPLE 105

7,7,10,10-Tetrafluoro-13-dehydroprostacyclin Methyl ester (M=$OCH_3$)

A solution of 3.9 mg of the iodo compound of Example 100 in 200 μl of toluene was degassed and flushed with $N_2$. 1,5-Diaza[5,4,0]bicycloundec-5-ene (DBU, 6.7 μl) was then syringed into the reaction vessel, which was immersed into a preheated oil bath at 90°. The reaction mixture was allowed to cool to room temperature and diluted with 0.5 ml of hexane:EtOAc (4:1). The precipitated solid was filtered through glass wool and the reaction vessel washed three times with the same solvent. The combined washings were cooled to 0° and washed with an equally cold pH 7 buffer and then with ice-cold distilled water. The organic extracts were dried quickly over $MgSO_4$-$K_2CO_3$ (1:1 W/W) and evaporated to yield 3.2 mg of the crude reaction product, which was purified by tlc (acetone-methylene chloride 3:7) to yield 7,7,10,10-Tetra-fluoro-13-dehydroprostacyclin methyl ester (1.4 mg).

EXAMPLE 106

7,7-Difluoro-13-dehydro-prostacyclin Methyl ester (M=$OCH_3$)

Following the procedure of Example 105 but substituting an equivalent amount of the 7,7-difluoro compound of Example 101 there is obtained the title compound.

EXAMPLE 107

4,4,7,7-Tetrafluoro-13-dehydroprostacyclin Methyl ester (M=$OCH_3$)

Following the procedure of Example 105 but substituting equivalent amount of the 4,4,7,7 compound of Example 102 there is obtained the title compound.

EXAMPLE 108

4,4,10,10-Tetrafluoro-13-dehydroprostacyclin Methyl ester (M=$OCH_3$)

Following the procedure of Example 105 but substituting an equivalent amount of the 4,4,10,10-tetrafluoro compound of Example 103 there is obtained the title compound.

EXAMPLE 109

5,10,10-Trifluoro-13-dehydroprostacylin Methyl ester (M=$OCH_3$)

Following the procedure of Example 105 but substituting an equivalent amount of the 5,10,10-trifluoro compound of Example 104 there is obtained the title compound.

EXAMPLE 110

7,7,10,10-Tetrafluoro-13-dehydroprostacyclin sodium salt (M=ONa)

7,7,10,10-Tetrafluoro-13-dehydroprostacyclin methyl ester (1.4 mg) in 0.2 ml of MeOH was stirred with 0.5N NaOH (0.70 ml), at room temperature for 2 hrs. Dry ice was then added to bring the pH of the solution down to 9. Most of the MeOH and water were blown down with $N_2$ and the residual gum was subjected to high vacuum for 18 hrs. The solid residue consisting of 7,7,10,10-tetrafluoroprostacyclin sodium salt (M=ONa) and Na$_2$CO$_3$ (for stabilization) is stored in the freezer.

EXAMPLE 111

7,7-Difluoro-13-dehydroprostacyclin sodium salt (M=ONa)

Following the procedure of Example 110 but substituting an equivalent amount of 7,7-difluoro methyl ester of Example 106 there is obtained the title compound (M=ONa).

EXAMPLE 112

4,4,7,7-Tetrafluoro-13-dehydroprostacyclin sodium salt (M=ONa)

Following the procedure of Example 110 but substituting an equivalent amount of the 4,4,7,7-tetrafluoro methyl ester of Example 107 there is obtained the title compound (M=ONa).

EXAMPLE 113

4,4,10,10-Tetrafluoro-13-dehydroprostacyclin sodium salt (M=ONa)

Following the procedure of Example 110 but substituting an equivalent amount of the 4,4,10,10-tetrafluoro methyl ester of Example 108 there is obtained the title compound (M=ONa).

EXAMPLE 114

5,10,10-Trifluoro-13-dehydroprostacyclin sodium salt (M=ONa)

Following the procedure of Example 110 but substituting an equivalent amount of the 5,10,10-trifluoro methyl ester of Example 109 there is obtained the title compound (M=ONa).

EXAMPLE 115

(15S)-1,2,3,4,5-Pentanor-6,9,11,15-tetrahydroxy-7,7,10,10-tetrafluoro-13-prostyne Trifluoroacetic acid (2.50 ml) was added in one portion to 146 mg of the t-butyl-triol-yne of Example 84 cooled to 0°–5°. The magnetically stirred solution was placed in a cold room at −15°, and the reaction followed by tlc. After completion (5 hrs), workup of the reaction was performed at 0°–5° with addition of saturated Na$_2$CO$_3$ solution (approx. 17 ml) until pH 10 followed by addition of 13 ml of MeOH. The contents were stirred at room temperature for 0.5 hrs, 10% HCl was added until the solution was neutral followed by addition of 50 ml of saturated NaCl solution. The aqueous solution was extracted with CHCl$_3$ (10×50 ml), the combined CHCl$_3$ extracts washed with saturated NaCl solution (2×250 ml), and the CHCl$_3$ layer dried over anhydrous Na$_2$SO$_4$. Filtration and evaporation of the solvent under vacuum gave 120 mg (100%) of the title compound.

EXAMPLE 116

(15S)-1,2,3,4,5-Pentanor-6,9,11,15-tetrahydroxy-7,7,10,10-tetrafluoro-13-prostene Lithium aluminum hydride (0.148 g, 4.10 mmole), the tetraol-yne of Example 46 (45 mg, 0.15 mmole) and 1.5 ml of dry THF were placed in a round bottom flask fitted with a spiral reflux condenser and drying tube. The contents were heated at gentle reflux in an oil bath maintained at 70°, and the reaction followed by glc. After 4 hrs, the reaction vessel was cooled to 0°–5° and 10% HCl was added until the evolution of gas ceased followed by addition of 30 ml of saturated NaCl solution. The aqueous solution was extracted with EtOAc (8×50 ml), the EtOAc extract washed with saturated NaCl solution (1×), and then dried over anhydrous Na$_2$SO$_4$. Filtration and removal of solvent under vacuum gave 40 mg (88%) of crude material. Column chromatography of the above isolated material with silica gel using EtOAc and EtOAc-MeOH (10:1) as the eluents gave 32 mg (80%) of the pure tetraol-ene as a slightly colored yellow oil.

EXAMPLE 117

(15S)-1,2,3,4,5-Pentanor-9,11,15-trihydroxy-7,7,10,10-tetrafluoro-13-prosten-6-oic acid 6,9-lactone Following the procedure of Example 86 but substituting an equivalent amount of the tetrol-ene of Example 116 there is obtained the title compound.

EXAMPLE 118

(15S)-1,2,3,4,5-Pentanor-9,11,15-trihydroxy-7,7,10,10-tetrafluoro-13-prosten-6-al hemiacetal Following the procedure of Example 88 but substituting an equivalent amount of the ene lactone of Example 117 for the yne lactone there is obtained the title compound.

EXAMPLE 119

7,7,10,10-Tetrafluoroprostaglandin F$_{2\alpha}$ tert-butyl ether

Following the procedure of Example 90 but substituting an equivalent amount of the ene hemiacetal of Example 118 for the yne hemiacetal there is obtained the title compound.

EXAMPLE 120

7,7,10,10-Tetrafluoroprostaglandin F$_{2\alpha}$

Following the procedure of Example 95 but substituting an equivalent amount of the 7,7,10,10-tetrafluoroprostaglandin F$_{2\alpha}$ tert-butyl ether of Example 119 there is obtained the title compound.

EXAMPLE 121

7,7,10,10-Tetrafluoro-5-iodo-9-oxidoprostaglandin F$_{1\alpha}$ Methyl ester

Following the procedure of Example 100 but substituting 7,7,10,10-tetrafluoro PGF$_{2\alpha}$ of Example 120 for its 13-dehydro derivative there is obtained the title compound.

EXAMPLE 122

7,7,10,10-Tetrafluoroprostacyclin Methyl ester

Following the procedure of Example 105 but substituting the ene iodo compound of Example 121 for the yne iodo compound there is obtained the title compound.

EXAMPLE 123

7,7,10,10-Tetrafluoroprostacyclin

Following the procedure of Example 110 but substituting 7,7,10,10-tetrafluoroprostacyclin methyl ester of Example 122 for the 13-dehydro methyl ester there is obtained the title compound.

EXAMPLE 124

7,7,10,10-Tetrafluoroprostacyclin

Following the procedure set forth in Example 84 but substituting an equivalent amount of dimethyl-3-t-butyloxy-1-nonynylalane for the dimethyl-3-t-butyloxy-1-octynylalane the corresponding homologous derivative is obtained.

EXAMPLE 125

Diethyl 2,2-Difluoroglutarate (b)

Diethyl 2-ketoglutarate (a, 10.06 g, 49.74 mmol), methylene chloride (150 ml), and water (0.5 ml) were combined in a stainless steel bomb under $N_2$ and cooled to $-78°$. Sulfur tetrafluoride (~90 g, 833 mmol) was condensed in a polypropylene bottle at $-78°$ and added to the reaction mixture. The bomb was sealed, then allowed to come to room temperature. After a total of 20 hrs, the bomb was vented through aqueous sodium hydroxide. The reaction mixture was worked up with methylene chloride, washing with aqueous sodium bicarbonate and brine. It yielded 11.38 g of crude yellow oil containing a white solid material. The white solid was filtered off and the oil distilled under reduced pressure through a Vigreux column. (bp 82°-96°, 5 mm). Total yield 6.27 g (57%) of the title compound as a light yellow oil. Silica gel tlc: $R_f$ 0.47 in EtOAc:Hexane 1:3.

EXAMPLE 126

Ethyl 4,4-Difluoro-5-hydroxypentanoate (c)

Diethyl 2,2-difluoroglutarate (2.50 g, 11.1 mmol) was dissolved in 400 ml of absolute ethanol. Sodium borohydride (0.53 g, 13.73 mmol) was added and the resulting solution was stirred vigorously under $N_2$ at room temperature for 7 hrs as the solution turned yellow. The ethanol was evaporated in vacuo, and the residue taken up in water EtOAc and acidified with 5% HCl. The ethyl acetate extract yielded after workup 1.50 g of the hydroxy-ester. It was filtered through a short column (50 g) of silica gel (eluted with ether) to give 1.30 g (64% yield) of the title compound as a colorless oil. Tlc on silica gel: $R_f$ 0.44 in EtOAc:hexane 1:3.

EXAMPLE 127

Ethyl 5-oxo-4,4-difluoro-n-pentanoate (d)

To a solution of oxalyl chloride (7.7 μl, 0.8 mmol) in 1.5 ml of $CH_2Cl_2$ was added at $-78°$ under $N_2$ a solution of dimethylsulfoxide (128 μl, 1.81 mmol) in 500 μl of $CH_2Cl_2$. After stirring for 10 min a solution of the difluoro alcohol c (109.9 mg, 0.60 mmol) in 1 ml of $CH_2Cl_2$ was added and the mixture allowed to remain at $-78°$ for 45 min. Triethylamine was then added (521 μl, 3.74 mmol) and after 10 min at $-78°$ the mixture was allowed to warm to room temperature. After addition of 1 ml of water $CH_2Cl_2$ was added and the organic layer extracted three times with 0.1N HCl and finally with water. Evaporation of the $CH_2Cl_2$ solution after drying over $Na_2SO_4$ yielded starting material (51.4 mg). Extraction of the aqueous solution with 5 portions of ethyl acetate yielded after drying over $Na_2SO_4$ and evaporation in vacuo 50.3 mg of the aldehyde d which existed mainly as the hydrate.

EXAMPLE 128

1,1-Difluoro-2,4-cis-dihydroxy-2,3-cis-3-carboxydifluoromethyl-2,5-trans-5-iodo-cyclopentane 4,2'-Lactone Following the procedure of Example 7 but substituting an equivalent amount of 1,1-difluoro-2,3-cis-2-hydroxy-3-carboxydifluoromethyl-$\Delta^4$-cyclopentane 2,2'-lactone of Example 76 in the reaction there is obtained the title compound.

EXAMPLE 129

2,4-cis-Dihydroxy-2,3-cis-3-carboxydifluoromethyl-2,5-trans-5-iodo-cyclopentane 4,2'-lactone Following the procedure of Example 7 but substituting an equivalent amount of 2,3-cis-2-hydroxy-3-carboxydifluoromethyl-$\Delta^4$-cyclopentene 2,2'-lactone of Example 77 in the reaction there is obtained the title compound.

EXAMPLE 130

(2R,3S,4S,5R)-1,1-Difluoro-2,4-dihydroxy-3-carboxydifluoromethyl-5-iodocyclopentane 4,2'-Lactone Following the procedure of Example 8 but substituting an equivalent amount of 1,1-difluoro-2,3-cis-2-hydroxy-3-carboxydifluoromethyl-$\Delta^4$-cyclopentene 2,2'-lactone in the reaction there is obtained the title compound.

EXAMPLE 131

(2S,3S,4S,5S)-2,4-Dihydroxy-3-carboxydifluoromethyl-5-iodocyclopentane 4,2'-Lactone Following the procedure of Example 8 but substituting an equivalent amount of 2,4-dihydroxy-3-carboxydifluoromethyl-5-iodocyclopentane 2,2'-lactone in the reaction there is obtained the title compound.

EXAMPLE 132

(2R,3S,4S,5R)-1,1-Difluoro-2-hydroxy-3-carboxydifluoromethyl-4,5-epoxycyclopentane 2,2'-Lactone Following the procedure of Example 10 but substituting an equivalent amount of the lactone of Example 130 in the reaction there is obtained the title compound.

EXAMPLE 133

(2S,3S,4S,5S)-2-Hydroxy-3-carboxydifluoromethyl-4,5-epoxycyclopentane 2,2'-Lactone Following the procedure of Example 10 but substituting an equivalent amount of the lactone of Example 131 there is obtained the title compound.

EXAMPLE 134

(2R,3S,4S,5R)-1,1-Difluoro-2-hydroxy-3[1',1'-difluoro-2'-hydroxyethyl]-4,5-epoxycyclopentane Following the procedure of Example 13 but substituting an equivalent amount of the lactone epoxide of Example 132 in the reaction there is obtained the title compound.

EXAMPLE 135

(2S,3S,4S,5S)-2-Hydroxy-3[1',1'-difluoro-2'-hydroxyethyl]-4,5-epoxycyclopentane

Following the procedure of Example 13 but substituting an equivalent amount of the lactone epoxide of Example 133 there is obtained the title compound.

EXAMPLE 136

1,2,3,4,5-Pentanor-6,9,11,15-tetrahydroxy-7,7,10,10-tetrafluoro-13-prostyne-15-tert-butyl ether Following the procedure of Example 16 but substituting an equivalent amount of the epoxydiol of Example 134 in the reaction there is obtained the title compound.

EXAMPLE 137

1,2,3,4,5-Pentanor-6,9,11,15-tetrahydroxy-7,7-difluoro-13-prostyne 15-tert-butyl ether Following the procedure of Example 16 but substituting an equivalent amount of the epoxy diol of Example 135 in the reaction there is obtained the title compound.

EXAMPLE 138

1,2,3,4,5-Pentanor-6,9,11,15-tetrahydroxy-13-prostyne 15-tert-butyl ether 9,11-diacetate 6-mesylate A solution of 135 mg of 1,2,3,4,5-pentanor-6,9,11,15-tetrahydroxy-13-prostyne-15-tert-butyl ether and 228 mg of trityl chloride in 1.8 ml of pyridine was allowed to remain at room temperature for 21 hrs. Chloroform was then added, the mixture washed with water and brine, the chloroform solution dried over sodium sulfate and evaporated to dryness in vacuo. Chromatography on 18 g of silica gel followed by elution with ether containing 0.1% of pyridine gave 152 mg of the mono-trityl ether tert-butyl ether diol. This material was dissoled in 3 ml of anhydrous pyridine and 1.5 ml of acetic anhydride and allowed to remain at room temperature for 18 hrs. At the end of this period 0.25 ml of water was added and the mixture extracted with ether. The ether solution was washed several times with water, dried over sodium sulfate and evaporated to dryness in vacuo leaving the 6-trityl ether 9,11-diacetate 15-tert-butyl ether as an oily residue, which was now treated with 3 ml of 90% acetic acid at room temperature for 18 hrs. The mixture was then taken up in methylene chloride and extracted with bicarbonate to remove acetic acid. The organic phase was dried over sodium sulfate and evaporated to dryness in vacuo. The resulting residue of the 9,11-diacetate 15-tert-butyl ether-6-ol was dissolved in 2 ml of pyridine and treated with 0.3 ml of methanesulfonyl chloride. The resulting mixture was allowed to remain at 5°–10° following which it was taken up in methylene chloride, the solution extracted with bicarbonate and water, dried over sodium sulfate and evaporated to dryness in vacuo. The residue consists of the title compound.

EXAMPLE 139

1,2,3,4,5-Pentanor-6,9,11,15-tetrahydroxy-10,10-difluoro-13-prostyne 15-tert-butyl ether 9,11-diacetate 6-mesylate Following the procedure of Example 138 but substituting the 10,10-difluoroprostyne of Example 17 in the reaction there is obtained the title compound.

EXAMPLE 140

1,2,3,4,5-Pentanor-6,9,11,15-tetrahydroxy-7,7,10,10-tetrafluoro-13-prostyne 15-tert-butyl ether 9,11-diacetate 6-mesylate Following the procedure of Example 138 but substituting the 7,7,10,10-tetrafluoroprostyne of Example 136 in the reaction there is obtained the title compound.

EXAMPLE 141

1,2,3,4,5-Pentanor-6,9,11,15-tetrahydroxy-7,7-difluoro-13-prostyne 15-tert-butyl ether 9,11-diacetate 6-mesylate Following the procedure of Example 138 but substituting the 7,7-difluoroprostyne of Example 137 in the reaction there is obtained the title compound.

EXAMPLE 142

1,2,3,4,5-Pentanor-9,11,15-trihydroxy-13-prostyne 15-tert-butyl ether 9,11-diacetate 6-triphenylphosphonium bromide A solution of the acetate mesylate of Example 138 (75 mg) and lithium bromide (250 mg) in 5 ml of methyl ethyl ketone is refluxed for 4 hrs. The mixture is taken up in dilute sodium bicarbonate and methylene chloride, the organic phase washed with sodium bicarbonate, the solution dried with $Na_2SO_4$ and the solvent evaporated in vacuo. The residual bromide (65 mg) is taken up in acetonitrile and after addition of an equivalent amount of $PPh_3$ is refluxed for 5 hrs. Removal of the solvent leaves the title compound.

EXAMPLE 143

1,2,3,4,5-Pentanor-9,11,15-trihydroxy-10,10-difluoro-13-prostyne 15-tert-butyl ether 9,11-diacetate 6-triphenylphosphonium bromide Following the procedure of Example 142 but substituting the 10,10-difluoroprostyne tosylate of Example 139 in the reaction there is obtained the title compound.

EXAMPLE 144

4,4-Difluoro-13-dehydroprostaglandin $F_{2\alpha}$ tert-butyl ether

A solution of 50 mg of the diacetate 6-triphenylphosphonium bromide of Example 142 in 5 ml of 0.2N HCl in acetonitrile-water 3:1 was heated under reflux for 30 min, the solution neutralized carefully with sodium hydroxide to pH 7 and evaporated to dryness in vacuo. The carefully dried salt was dissolved in 500 μl of DMSO and to it was added a solution of dimsyl sodium prepared from 16 mg of NaH as described in Example 31. The resulting mixture was stirred at 25° for 10 min and an equivalent amount of the difluoro aldehyde ester, ethyl 5-oxo-4,4-difluoro-n-pentanoate of Example 127 was added. The reaction mixture was then allowed to stir at 25° for 1 hr following which it was cooled in ice water and acidified with N/10 HCl to a pH of 1. Extraction with ethyl acetate yielded the title compound which was purified by tlc.

EXAMPLE 145

4,4,10,10-Tetrafluoro-13-dehydroprostaglandin $F_{2\alpha}$ tert-butyl ether

Following the procedure of Example 144 but substituting the 10,10-difluoro diacetate phosphonium bromide of Example 143 in the reaction there is obtained the title compound.

EXAMPLE 146

2,2,7,7-Tetrafluoro-13-dehydroprostaglandin F$_{2\alpha}$ tert butyl ether

Following the procedure of Example 144 but substituting an equivalent amount of the 7,7-difluoroprostyne of Example 85 in the reaction there is obtained the title compound.

EXAMPLE 147

2,2,7,7,10,10-Hexafluoro-13-dehydroprostaglandin F$_{2\alpha}$ tert butyl ether

Following the procedure of Example 144 but substituting an equivalent amount of the 7,7,10,10-tetrafluoroprostyne of Example 84 in the reaction there is obtained the title compound.

EXAMPLE 148

2,2,10,10-Tetrafluoro-13-dehydroprostaglandin F$_{2\alpha}$

Following the procedure of Example 36 but substituting an equivalent amount of the tert butyl ether of Example 144 there is obtained the title compound.

EXAMPLE 149

2,2,7,7-Tetrafluoro-13-dehydroprostaglandin F$_{2\alpha}$

Following the procedure of Example 36 but substituting an equivalent amount of the tert butyl ether of Example 146 there is obtained the title compound.

EXAMPLE 150

2,2,7,7,10,10-Hexafluoro-13-dehydroprostaglandin F$_{2\alpha}$

Following the procedure of Example 36 but substituting an equivalent amount of the tert butyl ether of Example 147 there is obtained the title compound.

EXAMPLE 151

2,2,10,10-Tetrafluoro-13-dehydroprostacyclin methyl ester

Following the reaction sequence described in Example 41 and 46 but substituting an equivalent amount of the 2,2,10,10-tetrafluoro PG of Example 148 there is obtained the title compound.

EXAMPLE 152

2,2,7,7-Tetrafluoro-13-dehydroprostacyclin methyl ester

Following the reaction sequence described in Example 41 and 46 but substituting an equivalent amount of the 2,2,7,-tetrafluoro PG of Example 149 there is obtained the title compound.

EXAMPLE 153

2,2,7,7,10,10-Hexafluoro-13-dehydroprostacyclin methyl ester

Following the reaction sequence described in Example 41 and 46 but substituting an equivalent amount of the 2,2,7,7,10,10-hexafluoro PG of Example 150 there is obtained the title compound.

EXAMPLE 154

2,2,10,10-Tetrafluoro-13-dehydroprostacyclin sodium salt

Following the procedure of Example 51 but substituting the product of Example 151 there is obtained the title compound.

EXAMPLE 155

2,2,7,7-Tetrafluoro-13-dehydroprostacyclin sodium salt

Following the procedure of Example 51 but substituting the product of Example 152 there is obtained the title compound.

EXAMPLE 156

2,2,7,7,10,10-Hexafluoro-13-dehydroprostacyclin sodium salt

Following the procedure of Example 51 but substituting the product of Example 153 there is obtained the title compound.

EXAMPLE 157

4,4-Difluoro-13-dehydroprostacyclin sodium salt

Following the procedures laid down in Examples 36, 41, 46 and 51 but substituting an equivalent amount of 4,4-difluoro-13-dehydro-PGF$_{2\alpha}$ tert butyl ether of Example 143 in this reaction sequence there is obtained the title compound.

EXAMPLE 158

4,4,10,10-Tetrafluoro-13-dehydroprostacyclin sodium salt

Following the procedure of Example 157 but substituting an equivalent amount of 4,4,10,10-tetrafluoro-PGF$_{2\alpha}$ tert butyl ether of Example 144 in this reaction sequence there is obtained the title compound. The invention may be variously otherwise embodied within the scope of the appended claims.

What is claimed is:

1. A compound of the formula:

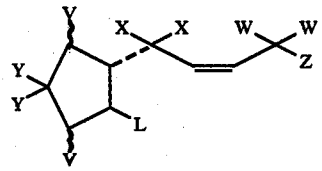

wherein Y, W and X may each be H or F; provided that at least one of Y, W and X is F; V may be hydroxy, acyloxy, lower alkoxy, hydroxy lower alkyl, or oxo: Z may be —Z$_1$—E wherein: Z$_1$ is (CH$_2$)$_g$—CH$_2$—CH$_2$—, or —(CH$_2$)$_g$—O—CH$_2$—, or —(CH$_2$)$_g$—CH$_2$—CF$_2$—, or trans—(CH$_2$)$_g$—CH=CH—; wherein g is 0, 1 or 2; and E is —COOX$_1$, wherein X$_1$ is hydrogen, lower alkyl, cycloalkyl, aralkyl, phenyl, phenyl substituted with chloro or lower alkyl, an alkali metal or a substituted ammonium cation; or —CH$_2$OH; or

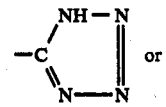 or

—CH$_2$NL$_2$L$_3$, wherein L$_2$ or L$_3$ are hydrogen, lower alkyl or —COOX$_1$ wherein X$_1$ is as defined above;
—COL$_4$, wherein L$_4$ is,
(a) amino of the formula —NR$_{21}$R$_{22}$, wherein R$_{21}$ and R$_{22}$ are hydrogen, alkyl of 1 to 12 carbon atoms inclusive, aralkyl of 7 to 12 carbon atoms inclusive, phenyl, phenyl substituted with 1, 2 or 3 chloro or alkyl substituents of 1 to 3 carbon atoms inclusive, or phenyl substituted with hydroxy carbonyl or alkoxy carbonyl of 1 to 4 carbon atoms inclusive; or
(b) carbonylamino of the formula, —NR$_{23}$COR$_{21}$, wherein R$_{23}$ is hydrogen or alkyl of 1 to 4 carbon atoms and R$_{21}$ is as defined above; or
(c) sulfonylamino of the formula —NR$_{23}$SO$_2$R$_{21}$, wherein R$_{21}$ and R$_{23}$ are as defined above; or
—COOL$_5$, wherein L$_5$ is p-substituted phenyl selected from the group consisting of:

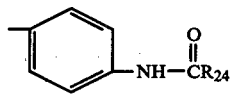

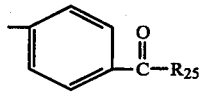

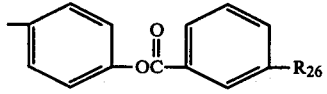

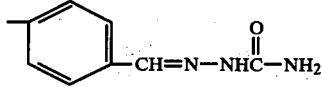

wherein R$_{24}$ is methyl, phenyl, acetamidophenyl, benzamidophenyl, or —NH$_2$; R$_{25}$ is methyl, phenyl, —NH$_2$, or methoxy; and R$_{26}$ is hydrogen or acetamido; and L is

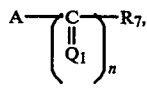

wherein n is 1 or 2; and A is —C≡C—, or trans— CH—C(Halogen)—; and

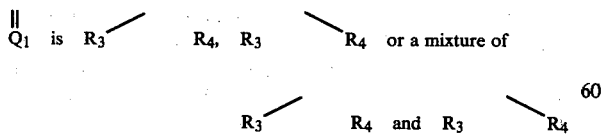

wherein R$_3$ and R$_4$ may be H, OH, alkoxy, acyloxy, or fluoro with the proviso that one of R$_3$ and R$_4$ is fluoro only when the other is fluoro or hydrogen and when taken together R$_3$ and R$_4$ is oxo; and R$_7$ may be:
(a) —(CH$_2$)$_g$—CH$_3$, wherein g is 3, 4 or 5;

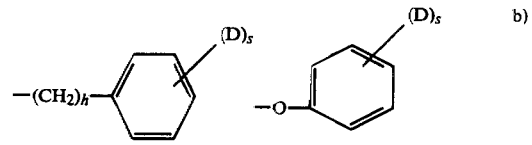

wherein h is 0, or 1; s is 0, 1, 2 or 3; and D is chloro, fluoro, trifluoromethyl, alkyl of one to 3 carbon atoms, inclusive, or with the proviso that not more than two D's are other than alkyl and the 1,5- and 1,15-lactones thereof; or
(c) CH$_2$OC═CH—CH$_2$CH$_3$; and wherein the acyl moieties herein are derived from hydrocarbon carboxylic acids of twelve carbon atoms or less; and wherein the aralkyl moieties herein are of from 7 to 12 carbon atoms.

2. A compound of the formula:

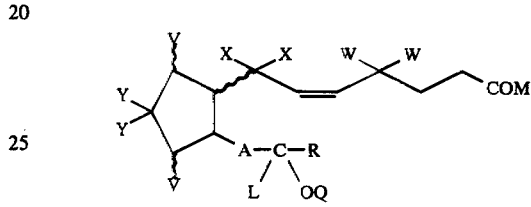

wherein Y, X, and W may be H or F; provided that at least one of Y, X, or W must be F; each V may be OH, acyloxy or alkoxy; A is —C≡C—; Q may be H, acyl or lower alkyl; L may be H or alkyl; R may be lower alkyl, alkenyl, aralkyl, substututed lower alkyl or substituted aralkyl; M may be OR$_1$ where R$_1$ is H, lower alkyl, aralkyl, an alkali metal or a substituted ammonium cation and wherein the acyl moieties herein are derived from hydrocarbon carboxylic acids of twelve carbon atoms or less; and wherein the aralkyl moieties herein are of from 7 to 12 carbon atoms.

3. A compound of the formula:

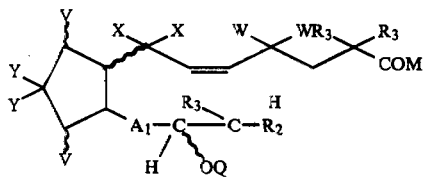

wherein A$_1$ is —C≡C—; R$_3$ is F or H; R$_2$ is lower alkyl, lower alkenyl, aralkyl or substituted aralkyl; M, Q, V, W, X, and Y, aree as hereinbefore defined in claim 2; and wherein the aralkyl moieties herein are of from 7 to 12 carbon atoms.

4. A compound of the formula:

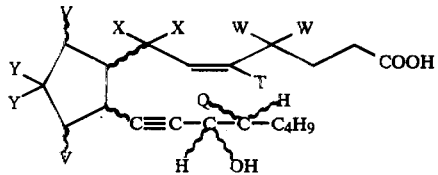

wherein Q is H or F; and Y, X, W, T, and V are as defined in claim 2.

5. 10,10-Difluoro-13-dehydroprostaglandin F$_{2\alpha}$.

* * * * *